United States Patent [19]

Krüger et al.

[11] 4,233,059
[45] Nov. 11, 1980

[54] 1,2,3-TRIAZOLE CARBOXYLIC ACID AMIDES AND BIOCIDAL COMPOSITIONS CONTAINING THE SAME

[75] Inventors: Hans-Rudolf Krüger; Friedrich Arndt; Dietrich Baumert; Hartmut Joppien; Ernst A. Pieroh; Reinhart Rusch, all of Berlin, Fed. Rep. of Germany

[73] Assignee: Schering Aktiengesellschaft, Berlin and Bergkamen, Fed. Rep. of Germany

[21] Appl. No.: 62,795

[22] Filed: Aug. 1, 1979

[30] Foreign Application Priority Data

Aug. 7, 1978 [DE] Fed. Rep. of Germany ....... 2834879

[51] Int. Cl.³ .................... C07D 249/04; A01N 9/12; A01N 9/14
[52] U.S. Cl. .......................... 71/92; /248.5; 424/248.52; 424/267; 424/269; 544/132; 546/210; 548/255; 260/245.5; 424/248.5
[58] Field of Search ..................... 544/132; 546/210; 548/255; 260/245.5; 71/92; 424/248.5, 248.52, 267, 269

[56] References Cited

PUBLICATIONS

Staub et al., *Chem. Abstracts*, v. 57, (1962), No. 4649h.

*Primary Examiner*—John D. Randolph
*Assistant Examiner*—R. W. Ramsuer
*Attorney, Agent, or Firm*—Michael J. Striker

[57] ABSTRACT

1,2,3-Triazole carboxylic acid amides, of the formula

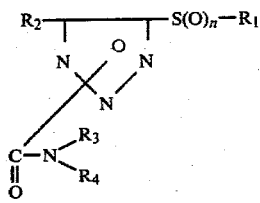

in which $R_1$, $R_2$, $R_3$, $R_4$ and $n$ have the meaning defined in the specification in connection with formula I. The compounds have a broad biocidal, particularly herbicidal, insecticidal, acaricidal, fungicidal and nematocidal activity. They have a high degree of selectivity towards agriculturally valuable plants.

152 Claims, No Drawings

1,2,3-TRIAZOLE CARBOXYLIC ACID AMIDES AND BIOCIDAL COMPOSITIONS CONTAINING THE SAME

BACKGROUND OF THE INVENTION

The invention relates to 1,2,3-triazole carboxylic acid amides and a process for making these compounds and relates also to biocidal composition containing these compounds, particularly compositions having herbicidal, insecticidal, acaricidal, fungicidal and/or nematocidal activity.

1,2,4-triazole derivatives having a herbicidal activity already known (U.S. Pat. No. 3,952,001). Among these N-ethyl-N-propyl-3(propylsulfonyl)-1H-1,2,4-triazole-1-carboxamide is distinguished by its action against gramineous weeds. This compound, however, has the shortcoming of an insufficient compatibility for agricultural plants such as maize and cotton.

1,2,3-triazole derivatives having the above-mentioned activity and the thus existing utility have not become known heretofore to the knowledge of these applicants.

It is, therefore, an object of the present invention to provide for new triazole derivatives and for a process for making them which have a broad spectrum of applications particularly in the area of plant protection.

SUMMARY OF THE INVENTION

This object is met by compounds constituted by 1,2,3-triazole carboxylic acid amides of the formula

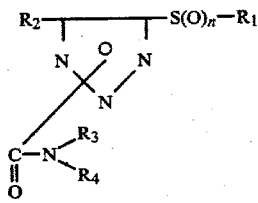

I, in which
- $R_1$ is $C_1-C_{10}$-alkyl, $C_2-C_8$-alkenyl or -alkinyl, or is an aryl $C_1-C_3$-alkyl which may be substituted in one or several positions by $C_1-C_6$-alkyl and/or halogen and/or $C_1-C_6$-alkoxy and/or nitro and/or trifluoromethyl;
- $R_2$ is hydrogen or $C_1-C_{10}$ alkyl of which the chain may be interrupted in one or several places by oxygen or sulfur and which may be substituted by halogen;
- $R_3$ and $R_4$ may be the same or different and may each be hydrogen, $C_1-C_{10}$-alkyl, $C_1-C_{10}$-alkyl which may be substituted by halogen or $C_1-C_3$-alkoxy, $C_2-C_3$-alkenyl or alkinyl, aryl-$C_1-C_3$-alkyl which may be substituted in one or several positions by $C_1-C_6$-alky and/or halogen and/or $C_1-C_6$-alkoxy and/or nitro and/or trifluoromethyl, a $C_3-C_8$-cycloaliphatic hydrocarbon group, a $C_3-C_8$ cycloaliphatic hydrocarbon group which may be substituted in one or several places by $C_1-C_6$-alkyl, an aromatic hydrocarbon group which may be substituted in one or several positions by $C_1-C_6$-alkyl and/or halogen and/or $C_1-C_6$-alkoxy and/or nitro and/or trifluoromethyl, or in which
- $R_3$ and $R_4$ together with the adjoining nitrogen atom may constitute a 3 to 7 member ring which may include further O—, S— or N— atoms, and in which
- n is 0, 1 or 2.

The compounds of the invention have a very broad biocidal activity. They are particularly distinguished by their herbicidal, insecticidal, acaricidal, fungicidal and/or nematocidal action which permits many different uses thereof in the area of plant protection.

Depending on the particular significance of the substituents there may thus be particularly important utilities in which the compounds exhibit a prominent action. Thus, the compounds may be used optionally as selective herbicides, plant growth regulators, insecticides, acaricides, fungicides or nematicides.

PREFERRED HERBICIDAL COMPOSITIONS

Among the compounds of the invention those are particularly distinguished by their herbicidal activity in which in the general formula I
- $R_1$ is alkyl of 1 to 10 carbon atoms, for instance methyl, ethyl, propyl, isopropyl, butyl, sec.-butyl, isobutyl, pentyl or isopentyl, or is aryl-$C_1-C_3$-alkyl which may be substituted by chlorine such as benzyl, 4-chlorobenzyl or 3,4-dichlorobenzyl,
- $R_2$ is hydrogen, methyl, ethyl, propyl, isopropyl, butyl or tert.-butyl,
- $R_3$ is alkyl, alkenyl or alkinyl of up to 6 carbon atoms which may be substituted by chlorine or methoxy, for instance methyl, ethyl, 2-chloroethyl, 2-methoxyethyl, propyl, isopropyl, 3-chloropropyl, 3-methoxypropyl, butyl, sec.-butyl, isobutyl, pentyl, isopentyl, hexyl, allyl, 2-methylallyl, propino-2-yl, or cycloalkyl, e.g., cyclohexyl, and
- $R_4$ is alkyl, alkenyl or alkinyl or up to 6 carbon atoms which may be substituted by chlorine or methoxy, for instance methyl, ethyl, 2-chloroethyl, 2-methoxyethyl, propyl, isopropyl, 3-methoxypropyl, 3-chloropropyl, butyl, sec.-butyl, isobutyl, pentyl, isopentyl, hexyl, allyl, 2-methylallyl, or propino-2-yl, or cycloalkyl, e.g. cyclohexyl, or is aryl-$C_1-C_3$-alkyl which may be substituted by chlorine or methyl, for instance benzyl, 4-chlorobenzyl or 4-methylbenzyl or is an aromatic hydrocarbon group which may be substituted by halogen or methyl, for instance phenyl, 4-chlorophenyl, 4-methylphenyl, or 4-fluorophenyl, or
- $R_3$ and $R_4$ together with the adjoining nitrogen atom constitute the morpholino-, piperidino-, pyrrolidino- or hexamethyleneimino group, and
- n is 2.

These compounds have the advantage over the prior art compounds that they have a broad range of selectivity towards agricultural plants quite apart from their high activity against mono- and a few dicotyl weeds. They also have a broad herbicidal activity when applied in the soil and can be used against mono- and dicotyl weeds in pre-emergence and post-emergence application. The compounds are effective also against weeds such as Avena fatua, Alopecurus myosuroides, Echinochloa crus galli, Digitaria sanguinalis, Cyperus esculentus, Sorghum halepense, Poa annua, Stellaria media, Senecio vulgaris, Amaranthus retroflexus, Polygonum lapathifolium and other weeds.

When used against weeds they are normally empolyed in amounts of 0.6 kg of active agent per about 2.5 acres up to 5 kg of active agent for the same area. The compounds of the invention in these cases are particularly selective against agricultural plants such as maize, cotton, potatoes, soy beans, peas and bush beans.

In addition, the compounds just discussed and also other compounds coming under the formula I have growth regulating properties.

The visually discernible morphological changes always presuppose a modification of the physiological and biochemical processes in the plant, for instance the compounds of the invention stimulate the following changes in the development of the plants:

Retardation of the vertical growth
Retardation of the root development
Intensification of the formation of plant pigments
Induction or promotion of the falling of the leaves.

The compounds of the invention can either be used alone or in mixture with each other or admixed with other active agents. If desired, other plant protection agents or pesticides may be added.

If a broadening of the activity range is intended it is possible also to add other herbicides. For instance, herbicidally active mixture components may be obtained from the group of the triazines, aminotriazoles, anilides, diazines, uraciles, aliphatic carboxylic acids and halogenated carboxylic acids, substituted benzoic acid and aryloxycarboxylic acids, hydrazides, amides, nitriles, esters of such carboxylic acids, carbamic acid- and thiocarbamic acid esters, urea derivatives, 1,3,6-trichlorobenzyloxypropanil and thiocyanate containing agents among others.

This reference to other additives should be understood to comprise also nonphytotoxic additives which in herbicides result in a synergistic activity increase such as wetting agents, emulsifiers, solvents and all the additives.

Preferred Insecticidal and Acaricidal Compounds

By their insecticidal and/or acaricidal activity are particularly distinguished those compounds in which in the formula I $R_1$ is methyl, ethyl, propyl, allyl, or propinyl-2-yl, $R_2$ is hydrogen, methyl, ethyl, propyl, butyl or tert.-butyl, $R_3$ is hydrogen or methyl, and $R_4$ is methyl and n is 0.

These compounds have a broad insecticidal and/or acaricidal activity. A particular advantage lies in their high initial action.

The compounds of the invention can be used against a multiplicity of economically very significant pests, particularly from the systems of the dipterons, coleopterans, rhynchotans and orthopterans.

The compounds discussed are particularly effective at the usual concentrations as used in industrial practice of 0.5 and less than 0.01%.

Particularly distinguished among the compounds of the invention is the 4-methyl-5-methylthio-1,2,3-triazole-1 (2,3)-carboxylic acid dimethylamide.

These compounds likewise can either be used alone or intermixed with each other or in mixture with other active agents. Depending on the particular purpose other plant protection agents may be added as well as activity increasing additives such as solvents, wetting agents and oils.

Preferred Nematicidal compositions

A nematicidal effect is possessed particularly by those compounds in which in the formula I
$R_1$ is alkyl of 1 to 10 carbon atoms, for instance methyl, ethyl, propyl, isopropyl, butyl, sec.-butyl, isobutyl, tert.-butyl, pentyl, isopentyl, allyl, 2-methylallyl, propine-2-yl, or is aryl-$C_1$-$C_3$-alkyl which may be substituted by chlorine, for instance benzyl, 4-chlorobenzyl or 3,4-dichlorobenzyl,
$R_2$ is hydrogen, methyl, ethyl, propyl, isopropyl, butyl, sec.-butyl, isobutyl or tert.-butyl,
$R_3$ is hydrogen, alkyl, alkenyl or alkinyl of up to 6 carbon atoms, for instance methyl, ethyl, propyl, isopropyl, butyl, sec.-butyl, tert.-butyl, allyl or propino-2-yl,
$R_4$ is alkyl, alkenyl or alkinyl with up to 6 carbon atoms for instance methyl, ethyl, propyl, isopropyl, butyl, sec.-butyl, isobutyl, tert.-butyl, allyl or propino-2-yl, and
n is 0.

These compounds have surprisingly no phytotoxic effect in the amounts used in practical application. Therefore negative impacts on the plant growth do not occur.

When used against nematodes the compounds are preferably used in amounts of 10 to 50 kg of active agent per about 2.5 acres of soil and are applied in a uniform manner and subsequently worked into the soil.

Among the phytopathogenic nematodes for which the compounds of the invention are useful are for instance the families of the migrating root nematodes Tylenchorhynchus, Pratylenchus, Paratylenchus, Heliocotylenchus, Xiphinema, Trichodorus and Longidorus; root gall nematodes as for instance *Meloidogyne incognita, Meloidogyne hapla, Meloidogyne arenaria*.

The active agents can be used for this purpose as such in the form of their formulations proper or in the form of application compositions made therefrom, such as solutions for actual use, emulsifiable concentrations, emulsions, suspensions, spray powders, pastes and granulates. The application is carried out in conventional form, for instance by pouring, spraying, gasifying, smoking, dusting, etc.

Preferred Fungicidal Compositions

A fungicidal effect is characteristic for all compounds of the general formula I and this both in treating the plants and in applying the compounds to the seeds of the plants. The compounds of the invention constitute a particular technical advance because they open up new alternative possibilities where a prior art fungicide either is no longer effective because of resistance of the fungus, or cannot be used for other reasons.

General Uses and Applications

The active agents or their mixtures are preferably applied in the form of compositions such as powders, dusting agents, granulates, solutions, emulsions or suspensions. Liquid and/or solid carrier materials, for instance diluents and, if desired, cross-linking agents, adherents promoting agents, emulsifiers and/or dispersants may be added.

Suitable liquid carrier materials are for instance water, aliphatic and aromatic hydrocarbons, such as benzene, toluene, xylene, cyclohexanone, isophorone, dimethylsulfoxyide, dimethylformamide and furthermore mineral oil fractions.

As solid carrier materials there are suited mineral earths, for instance tonsil, silica gel, talc, kaolin, attaclay, limestone, silicic acid and vegetable products such as flours.

There may also be added surface active agents as for instance calciumlignosulfonate, polyoxyethylenealkylphenyl-ether, naphthalenesulfone acids and their salts, phenolsulfone acids and their salt, formaldehyde condensation products, fatty alcohol sulfates and furthermore substituted benzosulfone acids and their salts. If the active agents are used for the pretreatment of the seed material, it is also possible to add dyestuffs in order to give the pretreated seed material a distinct color.

The ratio of the active agent or agents in the different compositions can be varied over a broad range. The compositions, for instance, may contain about 10 to 80% by weight of active agents, about 90 to 20% by weight of liquid or solid carrier materials and, if desired, up to 20% by weight of surface active agent in which case case a corresponding reduction of the carrier material takes place.

The application of the compositions can be effected in conventional manner, for instance with water as carrier material in spray amounts of about 100 to 1000 liter per about 2.5 acres. An application of the composition is possible in the so-called "low volume" or "ultra-low-volume process" as also in the form of so-called micro granulates.

Process of Making

The compounds which to the applicants' knowledge have not been described so far in the literature can be made by way of different processes.

A. 1,2,3-triazoles of the formula

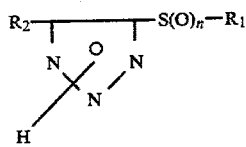  II are reacted with carbamoyl halides of the formula

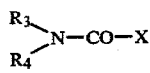  III in the presence of acid acceptors or they are reacted with isocyanates of the formula

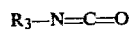  IV $R_3-N=C=O$ if desired, in the presence of a catalyst, preferably an organic base as, for instance, triethylamine.

B. Metal compounds of the formula

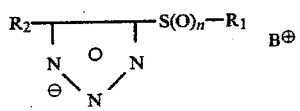  V may be reacted with carbamoylhalides of the formula

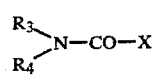  III or with isocyanates of the formula

  IV $R_3-N=C=O$

C. 1,2,3-triazole carboxylic acid halides of the formula

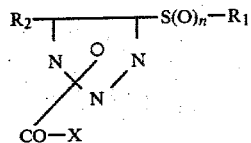  VI may be reacted with amines of the formula

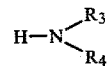  VII in the presence of acid acceptors.

D. Carbonylbis-1,2,3-triazoles of the formula

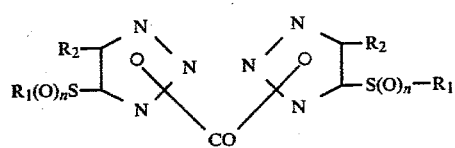  VIII may be reacted with amines of the formula

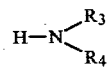  VII

In all these formulas wherever used $R_1$, $R_2$, $R_3$, $R_4$ and n have the same meaning as in the above-given formula I, and X is a halogen, preferably a chlorine atom and B is a univalent metal equivalent, preferably a sodium, potassium or lithium atom.

The reaction of the components takes place between 0° and 120° C., generally at room temperature. The components are used in about equimolar amounts. As reaction media there may be used polar organic solvents. The selection of the solvents or suspension agents depends on the kind of carbamoyl halides, of the kind of acid acceptors, on the metal compounds and the corresponding isocyanates used in the reaction.

As solvents or suspension agents there may, for instance be mentioned: acid nitriles, such as acetonitrile; ether, such as tetrahydrofuran and dioxane; acid amides, such as dimethylformamide; ketones, such as acetone; or chlorinated hydrocarbons, such as chloroform and tetracarbonchloride.

As acid acceptors there are suitable organic bases, for instance triethylamine, N,N-dimethylamine and pyridine or inorganic bases such as oxides, hydroxides and carbonates of the alkali earth- and alkali metals. Liquid bases such as pyridine and the use simultaneously as the solvents.

The 1,2,3-triazolcarboxylic acid amides made by the described processes which are liquids or solids may be isolated from a reaction mixture in conventional form, for instance by distilling off the solvent employed at atmospheric or reduced pressure or by precipitation with water.

Although the compounds of the invention in these processes are obtained in a highly pure form they can further be purified if desired for instance by recrystallization or by chromatography.

Starting Products

The 1,2,3-triazolecarboxylic acid halides which are used as starting products and have the formula

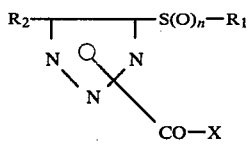 VI can be obtained from the triazoles of the above-given formula II by reaction with a carbonylhalide $COX_2$, preferably phosgene in conventional manner.

The carbonylbis-1,2,3-triazole which are used as starting products and have the formula

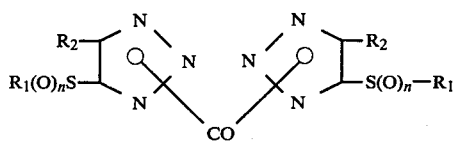 VIII can be obtained by reacting 1 mole of a triazole of the above-given formula II with about 0.5 moles of a carbonylhalogenide $COX_2$, preferably phosgene in conventional form. The reaction is preferably carried out in the presence of a suitable acid acceptor, for instance pyridine.

After forming the carbonylbis-1,2,3-triazole it is frequently preferably to react this product without isolating it with an amine of the formula

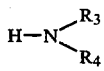

The other starting products are known or can be made by obvious prior art processes. For instance, the 1,2,3-triazoles of the formula II can be obtained by alkylating the corresponding 4-mercapto triazoles and then subjecting the reaction product preferably according to known procedures to a step-by-step oxidation.

The following examples will further illustrate the making of the starting products.

(A) Alkylthio-1,2,3-triazoles:

4-methyl-5-methylthio-1,2,3-triazole of the formula

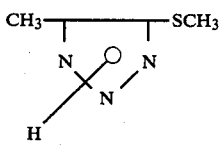

4.79 g (0.12 mole) of sodium hydroxide dissolved in 20 ml ethanol are added dropwise to a solution of 13.8 g (0.12 mole) of 5-mercapto-4-methyl-1,2,3-triazole in 60 ml ethanol. The addition is carried out at room temperature and the sodium hydroxide is applied as solution in 20 ml ethanol. Thereupon a reaction is effected at 30° C. with 19.85 g (0.14 mole) methyliodide and the reaction product after permitting to stand overnight at room temperature is then subjected to concentration in a vacuum at 40° C.

The residue is reacted with 150 ml water and is extracted with ether. The organic phase is dried on magnesium sulfate, filtrated and concentrated. The remaining crystals are recrystallized from cyclohexane.

The yield is 14.6 g=94.3% of the theoretical amount.
m.p.: 71°–71.5° C.
$C_4H_7N_3S$: molecular weight 129.19.

The following starting products were made in an analogous manner:

| Name | Physical Constants |
| --- | --- |
| 4-methylthio-1,2,3-triazole | m.p.: 47° C. |
| 4-ethylthio-1,2,3-triazole | $n_D^{20}$: 1.5449 |
| 4-propylthio-1,2,3-triazole | $n_D^{20}$: 1.5375 |
| 4-isopropylthio-1,2,3-triazole | $n_D^{20}$: 1.5331 |
| 4-butylthio-1,2,3-triazole | $n_D^{20}$: 1.5280 |
| 4-(1-methylpropylthio)-1,2,3-triazole | $n_D^{20}$: 1.5281 |
| 4-allylthio-1,2,3-triazole | $n_D^{20}$: 1.5561 |
| 4-isobutylthio-1,2,3-triazole | $n_D^{20}$: 1.5244 |
| 4-(2-propinylthio)-1,2,3-triazole | semicrystals |
| 4-benzylthio-1,2,3-triazole | m.p.: 61.5°–63.5° C. |

(B) Alkylsulfinyl-1,2,3-triazoles:

4-methylsulfinyl-1,2,3-triazole

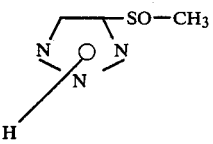

A solution of 57.5 g (0.5 mole) of 4-methylthio-1,2,3-triazole in 200 ml acetic acid is added dropwise within 10 minutes to 61.1 ml (0.6 mole) 30% hydrogen peroxide. The solution is then stirred for 30 minutes at a temperature of 40°–45° C. After standing overnight it is heated further for 30 minutes to 80° C., then cooled to room temperature whereupon the dark red reaction solution is decolorized with 0.2 g of sodium disulfite. The reaction solution is then concentrated in a vacuum at 40° C. The oily residue is recrystallized by digestion with diisopropylether.

Yield: 62.3 g=95% of the theoretical value
m.p.: 66°–67° C.
$C_3H_5N_3OS$: molecular weight 131.16.

(C) Alkylsulfonyl-1,2,3-triazoles:

4-propylsulfonyl-1,2,3-triazole

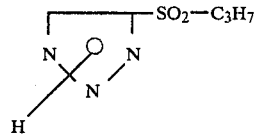

170.5 g (1.08 mole) of sodium permangamate are added batchwise within a period of 30 minutes at 45° to 55° C. to a solution of 103.2 g (0.72 mole) of 4-propylthio-1,2,3-triazole in 320 ml acetic acid and 420 ml water. The solution is then stirred for 10 minutes at 45° C. and reacted at 20° C. with a solution of 159.8 g (0.84 mole) of sodium disulfite in 500 ml water up to complete decolorization. Thereupon extraction is effected four times with 250 ml of acetic acid ester. The organic phase is then dried on magnesium sulfate, filtered and concentrated in a vacuum.

Yield: 119 g=94.5% of the theoretical value
$n_D^{20}$: 1.5085
$C_5H_9N_3O_2S$: molecular weight 175.21.

The following starting products have been made in analogous manner:

| Name | Physical Constants |
|---|---|
| 4-methylsulfonyl-1,2,3-triazole | m.p.: 101°–103° C. |
| 4-isopropylsulfonyl-1,2,3-triazole | $n_D^{20}$: 1.5067 |
| 4-benzylsulfonyl-1,2,3-triazole | m.p.: 163°–166° C. |
| 4-ethylsulfonyl-1,2,3-triazole | m.p.: 46°–48° C. |
| 4-butylsulfonyl-1,2,3-triazole | $n_D^{20}$: 1.4948 |
| 4-(1-methylpropylsulfonyl)-1,2,3-triazole | $n_D^{20}$: 1.4858 |
| 4-isobutylsulfonyl-1,2,3-triazole | m.p.: 71°–73° C. |

EXAMPLES OF THE COMPOUNDS OF THE INVENTION

The following Examples will illustrate the making of the 1,2,3-triazole carboxylic acid amides.

EXAMPLE 1

4-propylsulfonyl-1,2,3-triazole-1(2,3)-carboxylic acid propylamide (Compound No. 1)

8.75 g (0.05 mole) of 4-propylsulfonyl-1,2,3-triazole dissolved in 75 ml acetonitrile were reacted at room temperature with 5.55 g (0.055 mole) triethylamine. Upon stirring 8.18 g (0.05 mole) of dipropylcarbamoylchloride were then added at 70° C. within a period of 10 minutes. The solution was then further stirred for 2 hours at 70° C. and permitted to stand overnight. It was then concentrated in a vacuo at 40° C. The residue was reacted with 100 ml ice water and extracted with ether. The organic phase was thereafter washed with a 1% sodium bicarbanate solution, dried on magnesium sulfate, filtered and concentrated.

Yield: 12.6 g=18.4% of the theoretical value
$n_D^{20}$: 1.4964.

Probably the product is an isomer mixture of $N^1$ and $N^2$-carbamoyl products.

EXAMPLE 2

4-methyl-5-methylthio-1,2,3-triazole-1(2,3)-carboxylic acid dimethylamide (Compound no. 2)

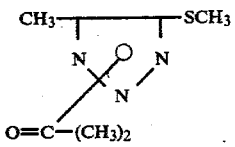

16.4 g (0.127 mole) of 4-methyl-5-methylthio-1,2,3-triazole, dissolved in 160 ml of tetrahydrofuran were reacted at room temperature with 15.35 g (0.152 mole) of triethylamine. Thereafter 16.3 g (0.152 mole) of dimethylcarbamoylchloride were added within a period of 5 minutes upon stirring at a temperature of 50° C. Stirring was then continued for 4 hours at 50° C. and the reaction product was permitted to stand for 1 day at room temperature. It was then concentrated in a vacuum at 40° C. The residue was reacted at 150 ml water and was twice extracted with 75 ml, each, of chloroform. The organic phase was then washed with a 1% sodium bi-carbonate solution, dried on magnesium sulfate, filtered and concentrated.

Yield: 23.5 g=92.5% of the theoretical value
$n_D^{20}$: 1.5370.

The product is a uniform isomer probably a $N^2$-carbamoyl product.

EXAMPLE 3

4-methylthio-1,2,3-triazole-1(2,3)-carboxylic acid methylamide (Compound No. 3)

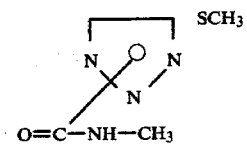

11.5 g (0.1 mol) of 4-methylthio-1,2,3-triazole were dissolved in 100 ml of tetrahydrofuran and then reacted with 6.27 g (0.11 mole) of methylisocyanate within a period of 3 minutes at 5° C. There were furthermore added as catalyst 0.1 ml of triethylamine. Subsequently, stirring was continued for 1 hour at 5° C. and then for another 1½ hour at room temperature. Concentration was then effected in a vacuum and 40° C. and the resulting residue (an isomer mixture) was recrystallized upon vigorous stirring from 500 ml water.

Yield: 8.7 g=50.5% of the theoretical value
m.p.: 107°–109° C. (decomposition).

The product is uniform isomer probably an $N^2$ carbamoyl product.

EXAMPLE 4

4-methylthio-1,2,3-triazole-1(2,3)-carboxylic acid methylamide (Compound No. 4)

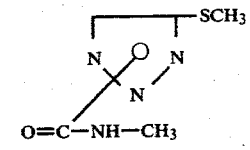

11.5 g (0.1 mole) of 4-methylthio-1,2,3-triazole were dissolved in 125 ml carbon tetrachloride and were then reacted with 6.27 g (0.11 mole) of methylisocyanate at room temperature within a period of 10 minutes. After standing overnight the crystals were removed by suction and further washed with a little carbontetrachloride. The crystals were then recrystallized from benzene/cyclohexane.

Yield: 12.2 g=70.9% of the theoretical value
m.p.: 109°–110° C. (decomposition)

The product is a uniform isomer, probably and $N^1$ carbamoyl product.

The further compounds of the invention were made in an analogous manner.

| Compound No. | Name | Physical Constants |
|---|---|---|
| 5 | 4-methylthio-1,2,3-triazole 1(2,3)-carboxylic acid methylamide (isomer mixture) | m.p.: 93° C. (decomposed) |
| 6 | 4-methylthio-1,2,3-triazole-1(2,3)-carboxylic acid anilide (isomer mixture) | m.p.: 86.5°–89° C. (decomposed) |

| Compound No. | Name | Physical Constants |
|---|---|---|
| 7 | 4-methylthio-1,2,3-triazole 1(2,3)-carboxylic acid ethylamide (isomer mixture) | semicrystalline |
| 8 | 4-methylthio-1,2,3-triazole-1(2,3)-carboxylic acid propylamide (isomer mixture) | $n_D^{20} = 1.5482$ |
| 9 | 4-methylthio-1,2,3-triazole-1(2,3)-carboxylic acid butylamide (isomer mixture) | $n_D^{20} = 1.5400$ |
| 10 | 4-methylthio-1,2,3-thiazole-1(2,3)-carboxylic acid cyclohexylamide (isomer mixture) | m.p.: 63°–71° C. |
| 11 | 4-methylthio-1,2,3-triazole-1(2,3)-carboxylic acid anilide ($N^1$ - isomer) | m.p.: 98°–100° C. |
| 12 | 4-methylthio-1,2,3-triazole-1(2,3)-carboxylic acid anilide ($N^2$ - isomer) | m.p.: 93°–95° C. |
| 13 | 4-methylthio-1,2,3-triazole-1(2,3)-carboxylic acid-(2-methylanilide) ($N^2$ - isomer) | m.p.: 80°–88° C. |
| 14 | 4-methylthio-1,2,3-triazole-1(2,3)-carboxylic-acid-(2-chloroanilide) ($N^2$ - isomer) | m.p.: 110° C. (decomposed) |
| 15 | 4-methylthio-1,2,3-triazole 1(2,3)-carboxylic acid-(3-methylanilide) ($N^1$ - isomer) | m.p.: 91°–92.5° C. (decomposed) |
| 16 | 4-methylthio-1,2,3-triazole 1(2,3)-carboxylic acid-(4-methylanilide) ($N^1$ - isomer) | m.p.: 108.5°–109.5° C. (decomposed) |
| 17 | 4-methylthio-1,2,3-triazole 1(2,3)-carboxylic acid-(3-chloroanilide) ($N^1$ - isomer) | m.p.: 106°–107° C. (decomposed) |
| 18 | 4-methylthio-1,2,3-triazole-1(2,3)-carboxylic acid-(4-chloroanilide) ($N^1$ - isomer) | m.p.: 109°–110° C. (decomposed) |
| 19 | 4-methylthio-1,2,3-triazole-1(2,3)-carboxylic acid allylamide ($N^1$ - isomer) | m.p.: 50°–55° C. |
| 20 | 4-methylthio-1,2,3-triazole-1(2,3)-carboxylic acid dimethylamide (isomer mixture) | $n_D^{20}$: 1.5569 |
| 21 | 4-ethylthio-1,2,3-triazole-1(2,3)-carboxylic acid methylamide (isomer mixture) | $n_D^{20}$: 1.5571 |
| 22 | 4-propylthio-1,2,3-triazole 1(2,3)-carboxylic acid methylamide (isomer mixture) | m.p.: 35°–38° C. |
| 23 | 4-isopropylthio-1,2,3-triazole-1(2,3)-carboxylic acid methylamide (isomer mixture) | $n_D^{20}$: 1.5432 |
| 24 | 4-butylthio-1,2,3-triazole 1(2,3)-carboxylic acid methyl amide (isomer mixture) | $n_D^{20}$: 1.5408 |
| 25 | 4-(1-methylpropylthio)-1,2,3-trizole-1(2,3)-carboxylic acid-methylamide (isomer mixture) | $n_D^{20}$: 1.5390 |
| 26 | 4-allylthio-1,2,3-triazole-1(2,3)-carboxylic acid methylamide (isomer mixture) | semicrystal |
| 27 | 4-butylthio-1,2,3-triazole-1(2,3)-carboxylic acid methylamide ($N^1$ - isomer) | m.p.: 75°–77° C. |
| 28 | 4-(1-methylpropylthio)-1,2,3-triazole-1(2,3)-carboxylic acid methylamide ($N^1$ - isomer) | m.p.: 66°–69° C. |
| 29 | 4-allylthio-1,2,3-triazole-1(2,3)-carboxylic acid methylamide ($N^1$ - isomer) | m.p.: 84°–85° C. |
| 30 | 4-ethylthio-1,2,3-triazole-1(2,3)-carboxylic acid methylamide ($N^1$ - isomer) | m.p.: 84.5°–86° C. |
| 31 | 4-propylthio-1,2,3-triazole-1(2,3)-carboxylic acid methylamide ($N^1$ - isomer) | m.p.: 75°–78° C. |
| 32 | 4-isopropylthio-1,2,3-triazole-1(2,3)-carboxylic acid methylamide ($N^1$ - isomer) | m.p.: 91°–92.5° C. |
| 33 | 4-isobutylthio-1,2,3-triazole-1(2,3)-carboxylic acid methylamide (isomer mixture) | $n_D^{20}$: 1.5382 |
| 34 | 4-(2-propinylthio)-1,2,3-triazole-1(2,3)-carboxylic acid methylamide) (isomer mixture) | semicrystal |
| 35 | 4-benzylthio-1,2,3-triazole-1(2,3)-carboxylic acid methylamide (isomer mixture) | m.p.: 50°–54° C. |
| 36 | 4-isobutylthio-1,2,3-triazole-1(2,3)-carboxylic acid methylamide ($N^1$ - isomer) | m.p.: 82°–83.5° C. |
| 37 | 4-(2-propinylthio)-1,2,3-triazole-1(2,3)-carboxylic acid methylamide ($N^1$ - isomer) | m.p.: 101°–102° C. |
| 38 | 4-benzylthio-1,2,3-triazole-1(2,3)-carboxylic acid methylamide ($N^1$ - isomer) | m.p.: 84°–85° C. |
| 39 | 4-methylsulfonyl-1,2,3-triazol-1(2,3)-carboxylic acid dimethylamide (isomer mixture) | m.p.: 73°–83° C. |
| 40 | 4-methylsulfonyl-1,2,3-triazole-1(2,3)-carboxylic acid methylamide (isomer mixture) | m.p.: 132°–134° C. |
| 41 | 4-methylsulfonyl-1,2,3-triazole-1(2,3)-carboxylic acid ethylamide (isomer mixture) | m.p.: 110°–111° C. |
| 42 | 4-methylsulfonyl-1,2,3-triazole-1(2,3)-carboxylic acid propylamide (isomer mixture) | m.p.: 66°–72° C. |
| 43 | 4-methylsulfonyl-1,2,3-triazole-1(2,3)-carboxylic acid butylamide (isomer mixture) | m.p.: 70°–72° C. |
| 44 | 4-methylsulfinyl-1,2,3-triazole-1(2,3)-carboxylic acid methylamide (isomer mixture) | m.p.: 95°–97° C. |
| 45 | 4-methylsulfinyl-1,2,3-triazole-1(2,3)-carboxylic acid ethylamide (isomer mixture) | $n_D^{20}$: 1.5370 |
| 46 | 4-methylsulfinyl-1,2,3-triazole-1(2,3)-carboxylic acid propylamide (isomer mixture) | $n_D^{20}$: 1.5288 |
| 47 | 4-methylsulfonyl-1,2,3-triazole-1(2,3)-carboxylic acid anilide (isomer mixture) | m.p.: 134°–137° C. |
| 48 | 4-methylsulfonyl-1,2,3-triazole-1(2,3)-carboxylic acid cyclohexylamide (isomer mixture) | m.p.: 96°–103° C. |
| 49 | 4-methylsulfonyl-1,2,3-triazole-1(2,3)-carboxylic acid (4-chloroanilide) (isomer mixture) | m.p.: 170°–171° C. |
| 50 | 4-methylsulfonyl-1,2,3-triazole-1(2,3)-carboxylic acid (4-methylanilide) (isomer mixture) | m.p.: 156°–158° C. |
| 51 | 4-methylsulfonyl-1,2,3-triazole-1(2,3)-carboxylic acid allylamide (isomer mixture) | m.p.: 91°–92.5° C. |
| 52 | 4-methyl-5-methylthio-triazole-1(2,3)-carboxylic acid methylamide ($N^2$ - isomer) | m.p.: 102°–106° C. |
| 53 | 4-methylsulfinyl-1,2,3-triazole-1(2,3)-carboxylic acid butylamide (isomer mixture) | $n_D^{20}$: 1.5128 |
| 54 | 4-methylsulfinyl-1,2,3-triazole-1(2,3)-carboxylic acid (4-methylanilide) (isomer mixture) | m.p.: 122°–123° C. |

| Compound No. | Name | Physical Constants |
|---|---|---|
| 55 | 4-methylsulfinyl-1,2,3-triazole-1(2,3)-carboxylic acid (4-chloroanilide) (isomer mixture) | m.p.: 150° C. (decomposed) |
| 56 | 4-methylsulfinyl-1,2,3-triazol-1(2,3)-carboxylic acid allylamide (isomer mixture) | $n_D^{20}$: 1.5365 |
| 57 | 4-methylsulfinyl-1,2,3-triazol-1(2,3)-carboxylic acid dimethylamide (isomer mixture) | $n_D^{20}$: 1.5391 |
| 58 | 4-methylsulfonyl-1,2,3-triazole-1(2,3)-carboxylic acid diethylamide (isomer mixture) | $n_D^{20}$: 1.5065 |
| 59 | 4-ispropylsulfonyl-1,2,3-triazole-1(2,3)-carboxylic acid methylamide (isomer mixture) | m.p.: 141°–149° C. |
| 60 | 4-isopropylsulfonyl-1,2,3-triazole-1(2,3)-carboxylic acid dimethylamide ($N^1$ - isomer) | m.p.: 112°–113° C. |
| 61 | 4-isopropylsulfonyl-1,2,3-triazole-1(2,3)-carboxylic acid dimethylamide ($N^2$ - isomer) | $n_D^{20}$: 1.5061 |
| 62 | 4-isopropylsulfonyl-1,2,3-triazole-1(2,3)-carboxylic acid diethylamide (isomer mixture) | $n_D^{20}$: 1.4909 |
| 63 | 4-propylsulfonyl-1,2,3-triazole-1(2,3)-carboxylic acid methylamide (isomer mixture) | m.p.: 99°–109° C. |
| 64 | 4-propylsulfonyl-1,2,3-triazole-1(2,3)-carboxylic acid dimethylamide (isomer mixture) | $n_D^{20}$: 1.5131 |
| 65 | 4-propylsulfonyl-1,2,3-triazole-1(2,3)-carboxylic acid diethylamide (isomer mixture) | $n_D^{20}$: 1.4992 |
| 66 | 4-propylsulfonyl-1,2,3-triazole-1(2,3)-carboxylic acid ethylamide (isomer mixture) | m.p.: 48°–60° C. |
| 67 | 4-propylsulfonyl-1,2,3-triazole-1(2,3)-carboxylic acid (N-ethyl-N-propyl)-amide (isomer mixture) | $n_D^{20}$: 1.5031 |
| 68 | 4-methylsulfonyl-1,2,3-triazole-1(2,3)-carboxylic acid (N-ethyl-N-propyl)-amide (isomer mixture) | $n_D^{20}$: 1.5081 |
| 69 | 4-methylsulfonyl-1,2,3-triazole-1(2,3)-carboxylic acid-N-ethylanilide (isomer mixture) | $n_D^{20}$: 1.5489 |
| 70 | 4-isopropylsulfonyl-1,2,3-triazole-1(2,3)-carboxylic acid N-ethylanilide (isomer mixture) | $n_D^{20}$: 1.5384 |
| 71 | 4-propylsulfonyl-1,2,3-triazole-1(2,3)-carboxylic acid N-ethylanilide (isomer mixture) | $n_D^{20}$: 1.5406 |
| 72 | 4-isopropylsulfonyl-1,2,3-triazole-1(2,3)-carboxylic acid (N-ethyl-N-propyl)-amide (isomer mixture) | $n_D^{20}$: 1.5028 |
| 73 | 4-isobutylthio-1,2,3-triazole-1(2,3)-carboxylic acid dimethylamide (isomer mixture) | $n_D^{20}$: 1.5439 |
| 74 | 4-isobutylthio-1,2,3-triazole-1(2,3)-carboxylic acid dimethylamide(isomer mixture) | $n_D^{20}$: 1.5321 |
| 75 | 4-butylsulfonyl-1,2,3-triazole-1(2,3)-carboxylic acid dimethylamide (isomer mixture) | $n_D^{20}$: 1,5119 |
| 76 | 4-butylsulfonyl-1,2,3-triazole-1(2,3)-carboxylic acid diethylamide (isomer mixture) | $n_D^{20}$: 1,5010 |
| 77 | 4-isobutylsulfonyl-1,2,3-triazole-1(2,3)-carboxylic acid dimethylamide (isomer mixture) | $n_D^{20}$: 1,5107 |
| 78 | 4-isobutylsulfonyl-1,2,3-triazole-1(2,3)-carboxylic acid diethylamide isomer mixture) | $n_D^{20}$: 1,4999 |
| 79 | 4-ethylsulfonyl-1,2,3-triazole-1(2,3)-carboxylic acid dimethylamide (isomer mixture) | m.p.: 79°–82° C. |
| 80 | 4-ethylsulfonyl-1,2,3-triazole-1(2,3)-carboxylic acid diethylamide (isomer mixture) | $n_D^{20}$: 1,5080 |
| 81 | 4-(1-methylpropylsulfonyl)-1,2,3-triazole-1(2,3)-carboxylic acid dimethylamide (isomer mixture) | $n_D^{20}$: 1,5110 |
| 82 | 4-benzylsulfonyl-1,2,3-triazole-1(2,3)-carboxylic acid diethylamide (isomer mixture) | m.p.: 90°–91° C. |
| 83 | 4-butylthio-1,2,3-triazole-1(2,3)-carboxylic acid diethylamide (isomer mixture) | $n_D^{20}$: 1,5242 |
| 84 | 4-(1-methylpropylsulfonyl)-1,2,3-triazole-1(2,3)-carboxylic acid diethylamide (isomer mixture) | $n_D^{20}$: 1,5419 |
| 85 | 4-benzylsulfonyl-1,2,3-triazole-1(2,3)-carboxylic acid dimethylamide (isomer mixture) | $n_D^{20}$: 1,5538 |
| 86 | 4-ethylthio-1,2,3-triazole-1(2,3)-carboxylic acid dimethylamide (isomer mixture) | $n_D^{20}$: 1,5458 |
| 87 | 4-ethylthio-1,2,3-triazole-1(2,3)-carboxylic acid diethylamide (isomer mixture) | $n_D^{20}$: 1,5351 |
| 88 | 4-isobutylthio-1,2,3-triazole-1(2,3)-carboxylic acid diethylamide (isomer mixture) | $n_D^{20}$: 1,5210 |
| 89 | 4-(1-methylpropylthio)-1,2,3-triazole-1(2,3)-carboxylic acid dimethylamide (isomer mixture) | $n_D^{20}$: 1,5331 |
| 90 | 4-(1-methylpropylthio)-1,2,3-triazole-1(2,3)-carboxylic acid diethylamide (isomer mixture) | $n_D^{20}$: 1,5235 |
| 91 | 4-benzylthio-1,2,3-triazole-1(2,3)-carboxylic acid dimethylamide (isomer mixture) | $n_D^{20}$: 1,5988 |
| 92 | 4-benzylthio-1,2,3-triazole-1(2,3)-carboxylic acid diethylamide (isomer mixture) | $n_D^{20}$: 1,5760 |
| 93 | 4-4-propylsulfonyl-1,2,3-triazole-1(2,3)-carboxylic acid propylamide (isomer mixture) | m.p.: 67°–69° C. |
| 94 | 4-propylsulfonyl-1,2,3-triazole-1(2,3)-carboxylic acid butylamide (isomer mixture) | m.p.: 76°–79° C. |
| 95 | 4-propylsulfonyl-1,2,3-triazole-1(2,3)-carboxylic acid isopropylamide (isomer mixture) | m.p.: 68°–72° C. |
| 96 | 4-propylsulfonyl-1,2,3-triazole-1(2,3)-carboxylic acid dibutylamide (isomer mixture) | $n_D^{20}$: 1,4909 |
| 97 | 4-propylsulfonyl-1,2,3-triazole-1(2,3)-carboxylic acid pyrrolidide (isomer mixture) | $n_D^{20}$: 1,5305 |
| 98 | 4-propylsulfonyl-1,2,3-triazole-1(2,3)-carboxylic acid piperidide (isomer mixture) | $n_D^{20}$: 1,5270 |
| 99 | 4-propylsulfonyl-1,2,3-triazole-1(2,3)-carboxylic acid | $n_D^{20}$: 1,5176 |

-continued

| Compound No. | Name | Physical Constants |
|---|---|---|
| | diallylamide (isomer mixture) | |
| 100 | 4-propylsulfonyl-1,2,3-triazole-1(2,3)-carboxylic acid morpholide (isomer mixture) | $n_D^{20}$: 1,5251 |
| 101 | 4-butylsulfonyl-1,2,3-triazole-1(2,3)-carboxylic acid (N-ethyl-N-propyl-amide (isomer mixture) | $n_D^{20}$: 1,4990 |
| 102 | 4-isobutylsulfonyl-1,2,3-triazole-1(2,3)-carboxylic acid-(N-ethyl-N-propyl)-amide (isomer mixture) | $n_D^{20}$: 1,4972 |
| 103 | 4-(1-methylpropylsulfonyl)-1,2,3-triazole-1(2,3)-carboxylic acid-(N-ethyl-N-propyl)-amide (isomer mixture) | $n_D^{20}$: 1,4990 |
| 104 | 4-propylsulfonyl-1,2,3-triazole-1(2,3)-carboxylic acid-N-ethyl-N-butyl)amide (isomer mixture) | $N_D^{20}$: 1,4971 |
| 105 | 4-propylsulfonyl-1,2,3-triazole-1(2,3)-carboxylic acid dipentyl-amide (isomer mixture) | $n_D^{20}$: 1,4880 |
| 106 | 4-propylsulfonyl-1,2,3-triazole-1(2,3)-carboxylic acid-N-ethyl-N-cyclohexyl)-amide (isomer mixture) | $n_D^{20}$: 1,5161 |
| 107 | 4-propylsulfonyl-1,2,3-triazole-1(2,3)-carboxylic acid diisopropylamide (isomer mixture) | $n_D^{20}$: 1,5010 |
| 108 | 4-ethylsulfonyl-1,2,3-triazole-1(2,3)-carboxylic acid-N-ethyl-N-propyl-amide (isomer mixture) | $n_D^{20}$: 1,4998 |
| 109 | 4-ethylsulfonyl-1,2,3-triazole-1(2,3)-carboxylic acid dipropylamide (isomer mixture) | m.p.: 60°–61° C. |
| 110 | 4-ethylsulfonyl-1,2,3-triazole-1(2,3)-carboxylic acid dibutyl-amide (isomer mixture) | $n_D^{20}$: 1,4931 |
| 111 | 4-butylsulfonyl-1,2,3-triazole-1(2,3)-carboxylic acid dipropylamide (isomer mixture) | $n_D^{20}$: 1,4949 |
| 112 | 4-butylsulfonyl-1,2,3-triazole-1(2,3)-carboxylic acid dibutylamide (isomer mixture) | $n_D^{20}$: 1,4900 |
| 113 | 4-(1-methylpropylsulfonyl) 1,2,3-triazole-1(2,3)-carboxylic acid dibutylamide (isomer mixture) | $n_D^{20}$: 1,4910 |
| 114 | 4-isobutylsulfonyl-1,2,3-triazole-1(2,3)-carboxylic acid dipropylamide (isomer mixture) | $n_D^{20}$: 1,4920 |
| 115 | 4-isobutylsulfonyl-1,2,3-triazole-1(2,3)-carboxylic acid dibutylamide (isomer mixture) | $n_D^{20}$: 1,4887 |
| 116 | 4-(1-methylpropyl)-sulfonyl-1,2,3-triazole-1(2,3)-carboxylic acid dipropylamide (isomer mixture) | $n_D^{20}$: 1,4946 |
| 117 | 4-(1-methylpropyl)-sulfonyl-1,2,3-triazole-1(2,3)-carboxylic acid diisopropylamide (isomer mixture) | $n_D^{20}$: 1,4971 |
| 118 | 4-butylsulfonyl-1,2,3-triazole-1(2,3)-carboxylic acid-(N-ethyl- (isomer mixture) | $N_D^{20}$: 1,4951 |
| 119 | 4-isobutylsulfonyl-1,2,3-triazole-1(2,3)-carboxylic acid (N-ethyl-N-butyl)-amide (isomer mixture) | $n_D^{20}$: 1,4943 |
| 120 | 4-(1-methylpropyl)-sulfonyl-1,2,3-triazole-1(2,3)-carboxylic acid-(N-ethyl-N-butyl)-amide (isomer mixture) | $n_D^{20}$: 1,4968 |
| 121 | 4-ethylsulfonyl-1,2,3-triazole-1(2,3)-carboxylic acid-(N-ethyl-N-cyclohexyl)-amide | $n_D^{20}$: 1,5160 |
| 122 | 4-isopropylsulfonyl-1,2,3-triazole-1(2,3)-carboxylic acid dipropylamide (isomer mixture) | m.p.: 58°–60° C. |
| 124 | 4-butylsulfonyl-1,2,3-triazole-1(2,3)-carboxylic acid (N-ethyl-N-cyclohexyl)-amide (isomer mixture) | $n_D^{20}$: 1,5111 |
| 125 | 4-(1-methylpropyl)-sulfonyl-1,2,3-triazole-1(2,3)-carboxylic acid-(N-ethyl-N-cyclohexyl)amide (isomer mixture) | $n_D^{20}$: 1,5100 |
| 126 | 4-propylsulfonyl-1,2,3-triazole-1(2,3)-carboxylic acid diisobutylamide (isomer mixture) | $n_D^{20}$: 1,5011 |
| 127 | 4-propylsulfonyl-1,2,3-triazole-1(2,3)-carboxylic acid dihexyl-amide (isomer mixture) | $n_D^{20}$: 1,4891 |
| 128 | 4-propylsulfonyl-1,2,3-triazole-1(2,3)-carboxylic acid-(N-ethyl-N-benzyl)-amide (isomer mixture) | $n_D^{20}$: 1,5444 |
| 129 | 4-propylsulfonyl-1,2,3-triazole-1(2,3)-carboxylic acid-(N-ethyl-N-isopropyl)-amide (isomer mixture) | |
| 130 | 4-propylsulfonyl-1,2,3-triazole-1(2,3)-carboxylic acid-N,N-hexamethyleneamide (isomer mixture) | $n_D^{20}$: 1,5272 |
| 131 | 4-propylsulfonyl-1,2,3-triazole-1(2,3)carboxylic acid-N-(2-cyanoethyl)-anilide (isomer mixture) | m.p.: 124° C. |
| 132 | 4-propylsulfonyl-1,2,3-triazole-1(2,3)-carboxylic acid-N-methyl-anilide (isomer mixture) | |
| 133 | 4-ethylsulfonyl-1,2,3-triazole-1(2,3)-carboxylic acid-(N-ethyl-N-butyl)-amide (isomer mixture) | $n_D^{20}$: 1,5002 |
| 134 | 4-isopropylfonyl-1,2,3-triazole-1(2,3)-carboxylic acid-(N-ethyl-N-butyl)-amide (isomer mixture) | deliquescent |
| 135 | 4-isobutylsulfonyl-1,2,3-triazole-1(2,3)-carboxylic acid-(N-ethyl-N-cyclohexyl)-amide (isomer mixture) | $n_D^{20}$: 1,5078 |
| 136 | 4-butylsulfonyl-1,2,3-triazole-1(2,3)-carboxylic acid-(N-ethyl-N-isopropyl)-amide (isomer mixture) | $n_D^{20}$: 1,4962 |
| 137 | 4-isobutylsulfonyl-1,2,3-triazole-1(2,3)-carboxylic acid-(N-ethyl-N-isopropyl)-amide (isomer mixture) | $n_D^{20}$: 1,4970 |
| 138 | 4-propylsulfinyl-1,2,3-triazole-1(2,3)-carboxylic acid diethylamide (isomer mixture) | $n_D^{20}$: 1,5192 |
| 139 | 4-propylsulfonyl-1,2,3-triazole-1(2,3)-carboxylic acid-bis(2-chloroethyl)amide (isomer mixture) | $n_D^{20}$: 1,5238 |
| 140 | 4-butylsulfonyl-1,2,3-triazole-1(2,3)-carboxylic acid-(N-ethyl-N-benzyl)-amide (isomer mixture) | $n_D^{20}$: 1,5429 |
| 141 | 4-(1-methylpropyl)-sulfonyl-1,2,3-triazole-1(2,3)-carboxylic acid-(N-ethyl-N-benzyl)-amide (isomer mixture) | $n_D^{20}$: 1,5392 |
| 142 | 4-isobutylsulfonyl-1,2,3-triazole-1(2,3)-carboxylic acid-(N-ethyl-N-benzyl)-amide (isomer mixture) | $n_D^{20}$: 1,5361 |
| 143 | 4-methylsulfonyl-1,2,3-triazole-1(2,3)-carboxylic acid-(N-ethyl-N-butyl)-amide | m.p.: 60°–62° C. |

| Compound No. | Name | Physical Constants |
|---|---|---|
| | (isomer mixture) | |
| 144 | 4-ethylthio-5-methyl-1,2,3-triazole-1(2,3)-carboxylic acid-(dimethyl)-amide (isomer mixture) | $n_D^{20}$: 1,5333 |
| 145 | 4-propylsulfonyl-5-methyl-1,2,3-triazole-1(2,3)-carboxylic acid-dipropylamide (isomer mixture) | $n_D^{20}$: 1,4967 |
| 146 | 4-propylsulfonyl-5-methyl-1,2,3-triazole-1(2,3)-carboxylic acid-(N-ethyl-N-isopropyl)-amide (isomer mixture) | $n_D^{20}$: 1,4967 |
| 147 | 4-(2-propinylthio-5-methyl-1,2,3-triazole-1(2,3)-carboxylic acid-dimethylamide (isomer mixture) | $n_D^{20}$: 1,5568 |
| 148 | 4-methylsulfonyl-1,2,3-triazole-1(2,3)-carboxylic acid-(N-ethyl-N-isopropyl)-amide (isomer mixture) | $n_D^{20}$: 1,4989 |
| 149 | 4-ethylsulfonyl-1,2,3-triazole-1(2,3)-carboxylic acid-(N-ethyl-N-isopropyl)-amide (isomer mixture) | $n_D^{20}$: 1,5000 |
| 150 | 4-(1-methyl-propyl)-sulfonyl-1,2,3-triazole-1(2,3)-carboxylic acid-(N-ethyl-N-isopropyl)-amide (isomer mixture) | $n_D^{20}$: 1,4959 |
| 151 | 4-ethylsulfonyl-1,2,3-triazole-1(2,3)-carboxylic acid-diisopropylamide (isomer mixture) | $n_D^{20}$: 1,4952 |
| 152 | 4-isobutylsulfonyl-1,2,3-triazole-1(2,3)-carboxylic acid-diisopropylamide (isomer mixture) | $n_D^{20}$: 1,4925 |
| 153 | 4-butylsulfonyl-1,2,3-triazole-1(2,3)-carboxylic acid diisopropylamide (isomer mixture) | $n_D^{20}$: 1,4935 |
| 154 | 5-methyl-4-propylsulfonyl-1,2,3-triazole-1(2,3)-carboxylic acid diisopropylamide (isomer mixture) | $n_D^{20}$: 1,4911 |
| 155 | 4-isopropylthio-5-methyl-1,2,3-triazole-1(2,3)-carboxylic acid dimethylamide (isomer mixture) | $n_D^{20}$: 1,5254 |
| 156 | 4-allylthio-5-methyl-1,2,3-carboxylic acid dimethylamide (isomer mixture) | $n_D^{20}$: 1,5439 |
| 157 | 4-(2-cyanoethylthio)-5-methyl-1,2,3-triazole-1 (2,3)-carboxylic acid dimethylamide (isomer mixture) | $n_D^{20}$: 1,5400 |
| 158 | 4-methylthio-5-propyl-1,2,3-triazole-1(2,3)-carboxylic acid-dimethylamide | $n_D^{20}$: 1,5292 |
| 159 | 5-ethyl-4-methylthio-1,2,3-triazole-1(2,3)-carboxylic acid-dimethylamide | $n_d^{20}$: 1,5370 |
| 160 | 5-isopropyl-4-methylthio-1,2,3-triazole-1(2,3)-carboxylic acid-dimethylamide | $n_D^{20}$: 1,5263 |
| 161 | 5-tert.-butyl-4-methylthio-1,2,3-triazole-1(2,3)-carboxylic acid dimethylamide | $n_D^{20}$: 1,5271 |

Physical Properties—Isomer Structure

The compounds of the invention are normally colorless and non-smelling oils or crystalline materials which have a moderate up to good solubility in aliphatic hydrocarbons, in halogenated hydrocarbons, such as chloroform and carbon tetrachloride, ketones, such as acetone; carboxylic acid amides, such as dimethylformamide, sulfoxides, such as dimethylsulfoxide, carboxylic acid nitriles, such as acetonitrile and lower alcohols, such as methanol and ethanol. They have a limited solubility in water. The compounds of the invention as shown in formula I may be present in the following isomeric structures:

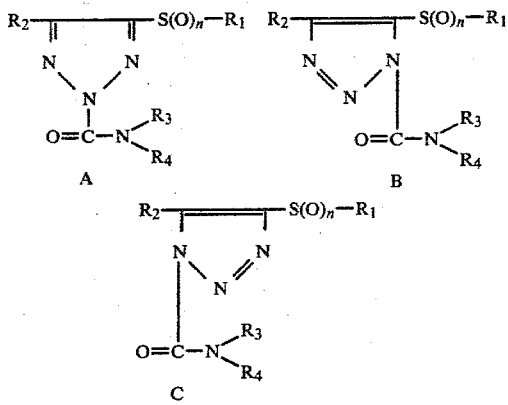

$R_1$, $R_2$, $R_3$, $R_4$ and n having the meaning as in formula I.

In the process of making there is possibly formed a mixture of the two isomers A and B if $R_2$ is hydrogen.

Compounds which consist exclusively of the structure shown above is A are possibly formed where $R_2$ is alkyl.

Since, however, the structure has not been completely clarified the compounds of the invention within the framework of the present specification and claims are designated as 1,2,3-triazole-1-(2,3)-carboxylic acid amides which is intended to mean that there may be present any of the structures identified above as A, B or C or an isomeric mixture thereof.

These mixtures could possibly be separated by conventional processes as, for instance, by a chromatographic procedure in which case the quantitative formation of one or the other isomer may be affected by the selection of a specific solvent. However, since the isomer mixtures have a particularly high biocidal activity the separation into individual isomers would be of no particular advantage.

Examples Illustrating Uses and Applications of the Compounds

EXAMPLE 5

The compounds listed in the following Table I were applied in a hothouse by spraying in a preemergence application in amounts of 5 kg of active agent per about 2.5 acres in an emulsion of 500 liters water to Digitaria s., Sorghum h, cotton and maize. Three weeks after treatment the results were evaluated on a scale from 0=to no action to 4=complete destruction of the plants.

As the table shows destruction of the weeds was accomplished while the agricultural plants were not damaged. The comparison compound contrary to these results destroyed also the agricultural plants.

TABLE I

| Compound of the Invention No. | maize | cotton | Digitaria s. | Sorghum h. |
|---|---|---|---|---|
| 1 | 0 | 0 | 4 | 4 |
| 58 | 0 | 0 | 4 | 4 |
| 61 | 0 | 0 | 4 | 4 |

TABLE I-continued

| Compound of the Invention No. | maize | cotton | Digi- taria s. | Sor- ghum h. |
|---|---|---|---|---|
| 62 | 0 | 0 | 4 | 4 |
| 64 | 0 | 0 | 4 | 4 |
| 65 | 0 | 0 | 4 | 4 |
| 67 | 0 | 0 | 4 | 4 |
| 68 | 0 | 0 | 4 | 4 |
| 69 | 0 | 0 | 4 | 4 |
| 70 | 0 | 0 | 4 | 4 |
| 71 | 0 | 0 | 4 | 4 |
| 72 | 0 | 0 | 4 | 4 |
| 75 | 0 | 0 | 4 | 4 |
| 76 | 0 | 0 | 4 | 4 |
| 77 | 0 | 0 | 4 | 4 |
| 78 | 0 | 0 | 4 | 4 |
| 79 | 0 | 0 | 4 | 4 |
| 80 | 0 | 0 | 4 | 4 |
| 81 | 0 | 0 | 4 | 4 |
| 82 | 0 | 0 | 4 | 4 |
| 84 | 0 | 0 | 4 | 4 |
| 85 | 0 | 0 | 4 | 4 |
| 96 | 0 | 0 | 4 | 4 |
| 99 | 0 | 0 | 4 | 4 |
| 101 | 0 | 0 | 4 | 4 |
| 102 | 0 | 0 | 4 | 4 |
| 103 | 0 | 0 | 4 | 4 |
| 104 | 0 | 0 | 4 | 4 |
| 105 | 0 | 0 | 4 | 4 |
| 106 | 0 | 0 | 4 | 4 |
| 107 | 0 | 0 | 4 | 4 |
| 108 | 0 | 0 | 4 | 4 |
| 109 | 0 | 0 | 4 | 4 |
| 110 | 0 | 0 | 4 | 4 |
| 111 | 0 | 0 | 4 | 4 |
| 112 | 0 | 0 | 4 | 4 |
| 113 | 0 | 0 | 4 | 4 |
| 114 | 0 | 0 | 4 | 4 |
| 115 | 0 | 0 | 4 | 4 |
| 142 | 0 | 0 | 4 | 4 |
| 143 | 0 | 0 | 4 | 4 |
| 144 | 0 | 0 | 4 | 4 |
| 145 | 0 | 0 | 4 | 4 |
| 146 | 0 | 0 | 4 | 4 |
| 147 | 0 | 0 | 4 | 4 |
| 148 | 0 | 0 | 4 | 4 |
| 149 | 0 | 0 | 4 | 4 |
| 150 | 0 | 0 | 4 | 4 |
| 151 | 0 | 0 | 4 | 4 |
| 152 | 0 | 0 | 4 | 4 |
| 153 | 0 | 0 | 4 | 4 |
| 154 | 0 | 0 | 4 | 4 |
| 155 | 0 | 0 | 4 | 4 |
| 156 | 0 | 0 | 4 | 4 |
| 157 | 0 | 0 | 4 | 4 |
| Comparison Compound | | | | |
| N-ethyl-4-propyl-3-(propyl-sulfonyl)-1H-1,2,4-triazole-1-carboxamide | 3 | 3 | 4 | 4 |
| No treatment | 0 | 0 | 0 | 0 |

EXAMPLE 6

The plants indicated in the following Table II were treated in a hothouse prior to emergence with the compounds also listed in the table in amounts of 3 kg of active agent per about 2.5 acres. Three weeks after treatment the compounds of the invention exhibited a high selectivity together with an excellent action against the weed. The comparison compound did not have the selective properties.

| Compound of the Invention No. | po- tatoe | maize | soy- bean | cot- ton | bush bean | pea | Elope- curus myo- soides | Avena fatua | Sen- ecio | Se- taria | Poa | Echino- chloa | Digit- aria | Cy- perus | Sor- ghum |
|---|---|---|---|---|---|---|---|---|---|---|---|---|---|---|---|
| 1 | 10 | 10 | 10 | 10 | 10 | 10 | 0 | 0 | 0 | 0 | 0 | 0 | 0 | 0 | 0 |
| 65 | 10 | 10 | 10 | 10 | 10 | 10 | 0 | 0 | 0 | 0 | 0 | 0 | 0 | 0 | 0 |
| 67 | 10 | 10 | 10 | 10 | 10 | 10 | 0 | 0 | 0 | 0 | 0 | 0 | 0 | 0 | 0 |
| 76 | 10 | 10 | 10 | 10 | 10 | 10 | 0 | 0 | 0 | 0 | 0 | 0 | 0 | 0 | 0 |
| Comparison Compound | | | | | | | | | | | | | | | |
| N-ethyl-4-propyl-3-(propylsulfonyl)-1H-1,2,4-triazole-1-carboxamide | 5 | 1 | 2 | 1 | 1 | 2 | 0 | 0 | 0 | 0 | 0 | 0 | 0 | 0 | 0 |
| Not treated | 10 | 10 | 10 | 10 | 10 | 10 | 10 | 10 | 10 | 10 | 10 | 10 | 10 | 10 | 10 |

| Compound of the Invention No. | maize | cotton | Digi- taria s. | Sor- ghum h. |
|---|---|---|---|---|
| 116 | 0 | 0 | 4 | 4 |
| 117 | 0 | 0 | 4 | 4 |
| 118 | 0 | 0 | 4 | 4 |
| 119 | 0 | 0 | 4 | 4 |
| 120 | 0 | 0 | 4 | 4 |
| 121 | 0 | 0 | 4 | 4 |
| 122 | 0 | 0 | 4 | 4 |
| 123 | 0 | 0 | 4 | 4 |
| 124 | 0 | 0 | 4 | 4 |
| 125 | 0 | 0 | 4 | 4 |
| 126 | 0 | 0 | 4 | 4 |
| 127 | 0 | 0 | 4 | 4 |
| 128 | 0 | 0 | 4 | 4 |
| 129 | 0 | 0 | 4 | 4 |
| 130 | 0 | 0 | 4 | 4 |
| 131 | 0 | 0 | 4 | 4 |
| 132 | 0 | 0 | 4 | 4 |
| 133 | 0 | 0 | 4 | 4 |
| 134 | 0 | 0 | 4 | 4 |
| 135 | 0 | 0 | 4 | 4 |
| 136 | 0 | 0 | 4 | 4 |
| 137 | 0 | 0 | 4 | 4 |
| 138 | 0 | 0 | 4 | 4 |
| 140 | 0 | 0 | 4 | 4 |
| 141 | 0 | 0 | 4 | 4 |

EXAMPLE 7

Young cotton plants in the stage where they have 5 to 7 leaves were treated with the compounds indicated below in Table III. The compounds were applied by spraying in an emulsion amount of 500 liters per about 2.5 acres. After a few days the percentage of the dropped leaves was determined. The results appear from the following table.

TABLE III

| Compound of the Invention No. | Doses in g active agent/ about 2.5 acres | defoliation in % |
|---|---|---|
| 2 | 500 | 48.0 |
| 58 | 500 | 12.0 |
| | 2000 | 50.0 |
| 65 | 500 | 13.6 |
| 67 | 500 | 28.0 |

EXAMPLE 8

Young cotton plants in the stage where they have 5 to 7 leaves were treated with the compound listed in the Table IV. For each treatment four plants were used which together had 24 to 25 leaves. The spray amount was 500 liters per about 2.5 acres.

After a few days the percentage of the dropped leaves was determined. The results appear from the table.

TABLE IV

| Compound of the Invention No. | Doses in g active agent/ about 2.5 acres | defoliation in % |
|---|---|---|
| 2 | 500 | 40.0 |
| Comparison Compound | | |
| Tri-n-butyl-trithio-phosphate | 500 | 4.7 |
| | 2000 | 4.7 |

EXAMPLE 9

Willow implants in the stage of about 11 to 14 leaves and provided with their roots were treated with the compounds indicated below in Table V in a manner as described in Example 8. For each treatment three plants were used having altogether 24 to 25 leaves.

TABLE V

| Compound of the Invention No. | Doses in g active agent/ about 2.5 acres | defoliation in % |
|---|---|---|
| 2 | 500 | 15.4 |
| 67 | 2000 | 61.5 |
| 68 | 2000 | 61.5 |
| Comparison compound | | |
| Tri-n-butyl-trithio-phosphate | 500 | 7.7 |

EXAMPLE 10

Cotton plants in the stage of 6 to 8 developed leaves were treated with the compounds indicated below in Table VI. The spray amount was 500 liters per about 2.5 acres. For each treatment four plants were used having together 28 leaves. After a few days the percentage of the dropped leaves was determined. The results appear from the following table.

TABLE VI

| Compound of the Invention No. | Doses in g active agent/ about 2.5 acres | defoliation in % |
|---|---|---|
| 2 | 2000 | 71.4 |
| 74 | 2000 | 59.3 |
| 80 | 2000 | 55.6 |

EXAMPLE 11

Cotton plants in the stage of 6 to 7 developed leaves were treated with the compounds indicated in Table VII. For each treatment four plants were used with a total of 25 to 26 meters. The spray amounts used were 500 liters per about 2.5 acres. After a few days the percentage of the dropped leaves was determined.

The results appear from the following table.

TABLE VII

| Compound of the Invention No. | Doses in g active agent/ about 2.5 acres | defoliation in % |
|---|---|---|
| 2 | 2000 | 72 |
| 58 | 2000 | 76 |
| 73 | 2000 | 88 |
| 84 | 2000 | 72 |
| 88 | 2000 | 80 |

EXAMPLE 12

The compounds appearing from the following Table VIII were applied as aqueous emulsions or suspensions in a concentration of active agent of 0.04%.

These compounds were sprayed in doses of 4 mg of sprayed amount per $cm^2$ into the tops of Petri dishes. To the thus formed spray deposits 25 adult Mediterranean fruit flies (Ceratitis capitata) per dish were exposed in the closed dishes under conditions of long-day duration. Criteria for the activity forms the mortality of the flies in percentage after 24 hours. The following table shows a comparison of the thus determined mortality percentages.

TABLE VIII

| Compound of the Invention No. | Concentration of active agent in % | Mortality in % after 24 hours |
|---|---|---|
| 2 | 0,04 | 100 |
| 3 | 0,04 | 100 |
| 4 | 0,04 | 68 |
| 5 | 0,04 | 95 |
| 20 | 0,04 | 100 |
| 21 | 0,04 | 90 |
| 22 | 0,04 | 52 |
| 23 | 0,04 | 90 |
| 24 | 0,04 | 45 |
| 25 | 0,04 | 80 |
| 26 | 0,04 | 75 |
| 27 | 0,04 | 95 |
| 28 | 0,04 | 75 |
| 29 | 0,04 | 60 |
| 30 | 0,04 | 56 |
| 31 | 0,04 | 52 |
| 32 | 0,04 | 20 |
| 52 | 0,04 | 100 |
| 57 | 0,04 | 79 |
| 73 | 0,04 | 100 |
| 74 | 0,04 | 100 |
| 86 | 0,04 | 100 |
| 87 | 0,04 | 100 |
| 89 | 0,04 | 100 |
| 144 | 0,04 | 100 |
| 147 | 0,04 | 100 |
| 158 | 0,04 | 100 |
| 159 | 0,04 | 100 |
| 160 | 0,04 | 100 |
| Untreated | | 0 |

EXAMPLE 13

The inventive compounds were applied as aqueous emulsions or suspensions with an active agent concentration of 0.04%.

With these active agent preparations the tops and bottoms of Petri dishes were sprayed with doses of 4 mg per $cm^2$. In the thus-formed deposits juvenile specimens of the German cockroach (Blattella germanica) were exposed in closed Petri dishes under conditions of long-day duration. For each dish there were used ten of the cockroaches which were 12 to 17 days old and they were exposed for a time of 48 hours.

The criterion for the activity was the mortality of the cockroaches in percentages after 48 hours. The following table shows the mortality percentage rate.

TABLE IX

| Compound of the Invention No. | Concentration of active agent in % | Mortality in % after 48 hours |
|---|---|---|
| 2 | 0,04 | 100 |
| 3 | 0,04 | 100 |
| 4 | 0,04 | 100 |
| 5 | 0,04 | 100 |
| 20 | 0,04 | 100 |
| 21 | 0,04 | 100 |
| 22 | 0,04 | 100 |
| 23 | 0,04 | 100 |
| 24 | 0,04 | 20 |
| 25 | 0,04 | 100 |
| 26 | 0,04 | 100 |
| 27 | 0,04 | 80 |
| 28 | 0,04 | 100 |
| 29 | 0,04 | 100 |
| 30 | 0,04 | 100 |
| 31 | 0,04 | 100 |
| 32 | 0,04 | 100 |
| 52 | 0,04 | 100 |
| 57 | 0,04 | 100 |
| 73 | 0,04 | 100 |
| 74 | 0,04 | 100 |
| 86 | 0,04 | 100 |
| 87 | 0,04 | 100 |
| 89 | 0,04 | 100 |
| 144 | 0,04 | 100 |
| 147 | 0,04 | 100 |
| 155 | 0,04 | 100 |
| 156 | 0,04 | 100 |
| 157 | 0,04 | 100 |
| 158 | 0,04 | 100 |
| 159 | 0,04 | 100 |
| 160 | 0,04 | 100 |

EXAMPLE 14

The compounds indicated below in Table X were used as aqueous emulsions or suspensions in a concentration of active agent of 0.04%. These compositions were then sprayed on potted broad beans (Vicia faba) so that the plants were dripping wet. The plants had before been infested heavily with the black bean louse (Aphis fabae).

The plants were then stored for 48 hours in the laboratory under conditions of long-day duration. The criterion for the activity was the mortality of the lice in percentage after 48 hours. The following table shows a comparison of the found mortality percentages.

TABLE X

| Compound of the Invention No. | Concentration of active agent in % | Mortality in % after 48 hours |
|---|---|---|
| 2 | 0,04 | 100 |
| 3 | 0,04 | 100 |
| 4 | 0,04 | 100 |
| 5 | 0,04 | 100 |
| 20 | 0,04 | 100 |
| 21 | 0,04 | 100 |
| 22 | 0,04 | 60 |
| 23 | 0,04 | 90 |
| 24 | 0,04 | 90 |
| 25 | 0,04 | 100 |
| 26 | 0,04 | 90 |
| 27 | 0,04 | 95 |
| 28 | 0,04 | 90 |
| 29 | 0,04 | 100 |
| 30 | 0,04 | 100 |
| 31 | 0,04 | 100 |
| 32 | 0,04 | 100 |
| 52 | 0,04 | 100 |
| 57 | 0,04 | 100 |
| 73 | 0,04 | 100 |

TABLE X-continued

| Compound of the Invention No. | Concentration of active agent in % | Mortality in % after 48 hours |
|---|---|---|
| 74 | 0,04 | 100 |
| 86 | 0,04 | 100 |
| 87 | 0,04 | 100 |
| 89 | 0,04 | 100 |
| 144 | 0,04 | 100 |
| 147 | 0,04 | 100 |
| 155 | 0,04 | 100 |
| 156 | 0,04 | 100 |
| 157 | 0,04 | 100 |
| 158 | 0,04 | 100 |
| 159 | 0,04 | 100 |
| 160 | 0,04 | 100 |

EXAMPLE 15

The compound of the invention indicated in Table XI and two comparison compounds were applied as aqueous suspensions in an active agent concentration of 0.0012%. These compositions were applied at a dose of 4 mg of spray per $cm^2$ to the bottoms and tops of Petri dishes. In the thus formed deposits juvenile specimens of the German cochroach (Blattella germanica) were exposed in closed Petri dishes under conditions of long-day duration. For each dish there were used ten of the cockroaches which were 12 to 17 days old and they were exposed for a time of 48 hours. The criterion for the activity was the mortality of the cochroaches in percentages after 48 hours. The following table shows the mortality percentages obtained.

TABLE XI

| Compound No. | Concentration of active agent in % | Mortality in % after 48 hours |
|---|---|---|
| 2 | 0.0012 | 100 |
| Comparison compound | | |
| o-isopropoxyphenyl-methylcarbamate | 0.0012 | 90 |
| 2,2-dimethyl-1,3-benzo-dioxol-4-yl-methylcarbamate | 0.0012 | 90 |

EXAMPLE 16

The compound of the invention indicated below in Table XII and the comparison compound were applied as aqueous suspensions in an active agent concentration of 0.00025%.

These compositions were sprayed in doses of 4 mg of spray amount per $cm^2$ into the tops and bottoms of Petri dishes. To the thus formed spray deposits ten specimens per Petri dish were exposed of the Asiatic cotton leaf bug (Dysdercus cingulatus) in closed Petri dishes under conditions of a long-day duration. The lice were exposed for 48 hours. They were in the juvenile stage, that is in third skin-shedding stage.

The criterion for the activity was the mortality of the leaf bugs in percentages after 48 hours. The following table shows a comparison of the mortality percentages found:

TABLE XII

| Compound of the Invention No. | Concentration of active agent in % | Mortality in % after 48 hours |
|---|---|---|
| 2 | 0.00025 | 95 |
| Comparison compound | | |
| 1-naphthyl-methyl- | | |

TABLE XII-continued

| Compound of the Invention No. | Concentration of active agent in % | Mortality in % after 48 hours |
|---|---|---|
| carbamate | 0.00025 | 60 |

EXAMPLE 17

The compounds of the invention and the comparison compounds shown in the following Table XIII were applied as aqueous emulsion at the indicated concentration. These compositions were sprayed at doses of 4 mg of spray amount per cm$^2$ into the tops and bottoms of Petri dishes. To the formed spray deposit ten specimens per Petri dish of the Asiatic cotton leaf bug (*Dysdercus cingulatus*) were exposed in the closed Petri dishes under conditions of a long-day duration. The exposure was for 42 hours and the insects were used in a juvenile stage, that is, in the third skin-shedding stage.

The criterion for the activity was the knockdown effect in percentage after 1, 30 and 60 minutes as well as the mortality of the leaf bugs after 42 hours.

TABLE XIII

| Compound of the Invention No. | Concentration of active agent in % | Knock-Down-effect in % after 1 min. | 30 min. | 60 min. | Mortality in % after 42 hrs. |
|---|---|---|---|---|---|
| 2 | 0,01 | 100 | 100 | 100 | 100 |
|  | 0,009 | 100 | 100 | 100 | 100 |
| 52 | 0,01 | — | 100 | 100 | 100 |
|  | 0,005 | — | — | 100 | 100 |
| Comparison compound |  |  |  |  |  |
| 2-methoxycarbonyl-1-methyl-nonyl-dimethylphosphate | 0,01 | 100 | 100 | 100 | 100 |
|  | 0,005 | — | 100 | 100 | 100 |
| 5-benzyl-3-furylmethyl(±)-cis,trans-chrysanthemate | 0,01 | — | 95 | 95 | 85 |
|  | 0,005 | — | — | 30 | 85 |

EXAMPLE 18

Seed Treatment of Barley Against Helminthosporium Spec.

Barley seeds were seeded into plant pots filled with earth. The seeds were infested by the *Helminthosporium gramineum*. The seeded material was partly untreated and partly treated as shown in Table I and was left for germination at a temperature below +16° C. After emergence illumination of the plants with light was effected for 12 hours daily. After about 5 weeks the infested plants were counted and in the same manner the total of the emerged plants. The fungicidal action was computed as follows:

$$100 - \frac{100 \cdot \text{infestation in treated plants}}{\text{infestation in untreated plants}} = \% \text{ activity}$$

TABLE XIV

| Compound of the Invention No. | g of active agent per 100 kg | % action |
|---|---|---|
| 2 | 20 | — |
|  | 50 | 100 |
| 4 | 20 | 69 |
|  | 50 | 94 |
| 7 | 20 | 54 |
|  | 50 | 90 |
| 19 | 20 | — |
|  | 50 | 90 |
| 20 | 20 | 97 |
|  | 50 | 100 |
| 21 | 20 | 82 |
|  | 50 | 93 |
| 25 | 20 | 67 |
|  | 50 | 90 |
| 28 | 20 | — |
|  | 50 | 70 |
| 29 | 20 | — |
|  | 50 | 70 |
| 30 | 20 | 87 |
|  | 50 | 98 |
| 31 | 20 | 56 |
|  | 50 | 79 |
| 32 | 20 | — |
|  | 50 | 58 |
| 33 | 20 | — |
|  | 50 | 70 |
| 34 | 20 | — |
|  | 50 | 87 |
| 35 | 20 | — |
|  | 50 | 90 |
| 37 | 20 | — |
|  | 50 | 94 |
| 38 | 20 | — |
|  | 50 | 77 |
| 39 | 20 | 100 |
|  | 50 | 100 |
| 52 | 20 | — |
|  | 50 | 70 |
| 57 | 20 | 100 |
|  | 50 | — |
| 58 | 20 | 95 |
|  | 50 | 100 |
| 59 | 20 | — |
|  | 50 | 70 |
| 60 | 20 | — |
|  | 50 | 100 |
| 61 | 20 | — |
|  | 50 | 100 |
| 64 | 20 | — |
|  | 50 | 100 |
| 143 | 20 | 76 |
|  | 50 | 87 |

EXAMPLE 19

Seed Treatment of Wheat Against Tilletia Caries

Oat seed material was contaminated with 3 g spores per kg of Tilletia caries which is the agent causing a stinking smuts. Untreated grains and grains treated as indicated in the following Table XV were pressed into Petri dishes filled with moist loam with their hairy end and were incubated at temperatures below +12° C. for a time of 3 days. The grains were subsequently removed and the Petri dishes with the stinking smuts spores left behind were further incubated at about 12° C. After 10 days the spores were examined regarding germination. The fungicidal activity was determined as follows:

$$100 - \frac{100 \cdot \text{germ percentage in treated grains}}{\text{germ percentage in untreated grains}} = \% \text{ activity}$$

TABLE XV

| Compound of the Invention No. | g of active agent per 100 kg | % action |
|---|---|---|
| 4 | 10 | 78 |
|   | 20 | 93 |
| 19 | 10 | — |
|   | 20 | 90 |
| 28 | 10 | — |
|   | 20 | 90 |
| 29 | 10 | — |
|   | 20 | 90 |
| 30 | 10 | — |
|   | 20 | 90 |
| 31 | 10 | 68 |
|   | 20 | 100 |
| 32 | 10 | 27 |
|   | 20 | 100 |
| 33 | 10 | — |
|   | 20 | 70 |
| 34 | 10 | — |
|   | 20 | 72 |
| 35 | 10 | — |
|   | 20 | 87 |
| 36 | 10 | — |
|   | 20 | 87 |
| 37 | 10 | — |
|   | 20 | 82 |
| 38 | 10 | 85 |
|   | 20 | 94 |
| 40 | 10 | — |
|   | 20 | 90 |
| 59 | 10 | — |
|   | 20 | 90 |
| 61 | 10 | — |
|   | 20 | 70 |
| 74 | 10 | — |
|   | 20 | 90 |
| 82 | 10 | — |
|   | 20 | 90 |
| 83 | 10 | — |
|   | 20 | 90 |
| 88 | 10 | — |
|   | 20 | 90 |
| 89 | 10 | — |
|   | 20 | 90 |
| 90 | 10 | — |
|   | 20 | 90 |
| 91 | 10 | — |
|   | 20 | 90 |
| 92 | 10 | — |
|   | 20 | 90 |
| 95 | 10 | — |
|   | 20 | 90 |
| 96 | 10 | — |
|   | 20 | 90 |
| 97 | 10 | — |
|   | 20 | 90 |
| 127 | 10 | — |
|   | 20 | 90 |
| 128 | 10 | — |
|   | 20 | 90 |
| 129 | 10 | — |
|   | 20 | 90 |
| 130 | 10 | — |
|   | 20 | 90 |
| 133 | 10 | — |
|   | 20 | 90 |
| 134 | 10 | — |
|   | 20 | 90 |
| 135 | 10 | — |
|   | 20 | 90 |
| 136 | 10 | — |
|   | 20 | 90 |
| 137 | 10 | — |
|   | 20 | 90 | table XV-continued

| Compound of the Invention No. | g of active agent per 100 kg | % action |
|---|---|---|
| 138 | 10 | — |
|   | 20 | 90 |
| 144 | 10 | 50 |
|   | 20 | 90 |
| 145 | 10 | 92 |
|   | 20 | 90 |
| 146 | 10 | 12 |
|   | 20 | 90 |
| 147 | 10 | 53 |
|   | 20 | 90 |
| 149 | 10 | — |
|   | 20 | 90 |
| 150 | 10 | — |
|   | 20 | 90 |

EXAMPLE 20

Spray Treatment of Rice Seedlings Against Piricularia Oryzae

Young rice plants were tripped to be dripping wet with the compounds given in the following Table XVI in the concentrations also indicated. After the spray deposits had been dried the treated plants and also untreated plants were inoculated in a hothouse in a humid atmosphere at +25° to +27° C. The inoculation was effected by spraying with a suspension of spores in an amount of about 200,000/ml of the Piricularia oryzae which is the agent causing the left spot disease. After 5 days it was determined which percentage of the leaf surface had been infected. From these infection figures the fungicidal activity was determined as follows:

$$100 - \frac{100 \cdot \text{infestation in treated plants}}{\text{infestation in untreated plants}} = \% \text{ activity}$$

TABLE XVI

| Compound of the Invention No. | % of active agent (sprayed dripping wet) | % action |
|---|---|---|
| 2 | 0,1 | 91 |
|   | 0,02 | 65 |
|   | 0,004 | — |
| 16 | 0,1 | 80 |
|   | 0,02 | — |
|   | 0,004 | — |
| 20 | 0,1 | 85 |
|   | 0,02 | — |
|   | 0,004 | — |
| 33 | 0,1 | 65 |
|   | 0,02 | — |
|   | 0,004 | — |
| 35 | 0,1 | 65 |
|   | 0,02 | — |
|   | 0,004 | — |
| 52 | 0,1 | 90 |
|   | 0,02 | — |
|   | 0,004 | — |
| 60 | 0,1 | 70 |
|   | 0,02 | — |
|   | 0,004 | — |
| 61 | 0,1 | 91 |
|   | 0,02 | 58 |
|   | 0,004 | — |
| 65 | 0,1 | 92 |
|   | 0,02 | 57 |
|   | 0,004 | — |
| 67 | 0,1 | 100 |
|   | 0,02 | 60 |
|   | 0,004 | — |
| 68 | 0,1 | 90 |
|   | 0,02 | — |
|   | 0,004 | — |
| 69 | 0,1 | 93 |

TABLE XVI-continued

| Compound of the Invention No. | % of active agent (sprayed dripping wet) | % action |
|---|---|---|
| | 0,02 | 45 |
| | 0,004 | — |
| 70 | 0,1 | 89 |
| | 0,02 | — |
| | 0,004 | — |
| 71 | 0,1 | 93 |
| | 0,02 | 55 |
| | 0,004 | — |
| 72 | 0,1 | 87 |
| | 0,02 | — |
| | 0,004 | — |
| 73 | 0,1 | 98 |
| | 0,02 | 80 |
| | 0,004 | 45 |
| 74 | 0,1 | 97 |
| | 0,02 | 75 |
| | 0,004 | 45 |
| 75 | 0,1 | 97 |
| | 0,02 | 87 |
| | 0,004 | 73 |
| 76 | 0,1 | 93 |
| | 0,02 | 80 |
| | 0,004 | 65 |
| 77 | 0,1 | 98 |
| | 0,02 | 87 |
| | 0,004 | 60 |
| 78 | 0,1 | 93 |
| | 0,02 | 75 |
| | 0,004 | 45 |
| 79 | 0,1 | 90 |
| | 0,02 | — |
| | 0,004 | — |
| 80 | 0,1 | 90 |
| | 0,02 | — |
| | 0,004 | — |
| 81 | 0,1 | 90 |
| | 0,02 | — |
| | 0,004 | — |
| 82 | 0,1 | 90 |
| | 0,02 | — |
| | 0,004 | — |
| 83 | 0,1 | 90 |
| | 0,02 | — |
| | 0,004 | — |
| 85 | 0,1 | 99 |
| | 0,02 | 87 |
| | 0,004 | 80 |
| 86 | 0,1 | 96 |
| | 0,02 | 20 |
| | 0,004 | 10 |
| 88 | 0,1 | 80 |
| | 0,02 | 35 |
| | 0,004 | 20 |
| 89 | 0,1 | 87 |
| | 0,02 | — |
| | 0,004 | — |
| 91 | 0,1 | 94 |
| | 0,02 | 87 |
| | 0,004 | 62 |
| 92 | 0,1 | 91 |
| | 0,02 | 73 |
| | 0,004 | 31 |
| 96 | 0,1 | 100 |
| | 0,02 | 89 |
| | 0,004 | 54 |
| 100 | 0,1 | 75 |
| | 0,02 | 69 |
| | 0,004 | — |
| 101 | 0,1 | 94 |
| | 0,02 | 62 |
| | 0,004 | 12 |
| 128 | 0,1 | 98 |
| | 0,02 | 65 |
| | 0,004 | 30 |
| 129 | 0,1 | 98 |
| | 0,02 | 50 |
| | 0,004 | 25 |
| 132 | 0,1 | 99 |
| | 0,02 | 50 |
| | 0,004 | 57 |
| 133 | 0,1 | 100 |
| | 0,02 | 89 |
| | 0,004 | 65 |
| 134 | 0,1 | 100 |
| | 0,02 | 85 |
| | 0,004 | 78 |
| 135 | 0,1 | 100 |
| | 0,02 | 100 |
| | 0,004 | 93 |
| 136 | 0,1 | 100 |
| | 0,02 | 80 |
| | 0,004 | 70 |
| 137 | 0,1 | 100 |
| | 0,02 | 80 |
| | 0,004 | 30 |
| 138 | 0,1 | 99 |
| | 0,02 | 86 |
| | 0,004 | 75 |
| 140 | 0,1 | 83 |
| | 0,02 | — |
| | 0,004 | — |
| 141 | 0,1 | 67 |
| | 0,02 | — |
| | 0,004 | — |
| 142 | 0,1 | 71 |
| | 0,02 | 17 |
| | 0,004 | — |
| 143 | 0,1 | 90 |
| | 0,02 | — |
| | 0,004 | — |
| 144 | 0,1 | 90 |
| | 0,02 | — |
| | 0,004 | — |
| 145 | 0,1 | 90 |
| | 0,02 | — |
| | 0,004 | — |
| 146 | 0,1 | 90 |
| | 0,02 | — |
| | 0,004 | — |
| 155 | 0,1 | 90 |
| | 0,02 | — |
| | 0,004 | — |
| 156 | 0,1 | 90 |
| | 0,02 | — |
| | 0,004 | — |

EXAMPLE 21

Spray Treatment of Tomato Seedlings Against Botrytis Cinerea

Young tomatoe plants were sprayed so as to be dripping wet with the compounds indicated in the following Table XVII at the concentration likewise indicated. After drying of the spray deposit the treated plants and also untreated plants were inoculated by spraying with a suspension of spores (about 1 million spores per ml of a fruit juice solution) of Botrytis cinera which is the agent causing the gray mold. The inoculation was effected in a hot house in a wet atmosphere at about 20° C. After the collapse of the untreated plants (the infestation in these plants was 100%) the degree of infestation of the treated plants was determined and the fungicidal action was calculated as follows:

$$100 - \frac{100 \cdot \text{infestation in treated plants}}{\text{infestation in untreated plants}} = \% \text{ action}$$

TABLE XVII

| Compound of the Invention No. | % of active agent (sprayed dripping wet) | % activity |
|---|---|---|
| 20 | 0.025 | 50 |
| 59 | 0.025 | 72 |

TABLE XVII-continued

| Compound of the Invention No. | % of active agent (sprayed dripping wet) | % activity |
|---|---|---|
| 64 | 0.025 | 78 |

EXAMPLE 22

Threshold Concentration Test Regarding Root Gall Nematodes (Meloidogyne Sp.)

A 20% powder composition of active agents was distributed uniformly in a soil which had been heavily infested with root gall nematodes. After a waiting time of 3 days the treated soil was spread out in two ceramic vessels of a capacity of 0.5 liters and 10 grains of cucumber seeds of the type "Guntruud" were laid into each dish. There followed a germination time of 28 days in a hothouse at a temperature of 24° to 27° C. The cucumber roots were then washed out and were examined in a water bath regarding nematode infestation. The reduction of infestation by the compounds of the invention as compared with untreated controls was determined in percentage as appears from Table XVIII. This table also shows the compounds of the invention, the amounts, and the reduction in infestation.

Nematocidal activity was calculated as follows:

$$A - B/A \cdot 100$$

wherein A is the infestation in the untreated control material and B is the infestation after treatment.

Threshold concentration test
Test namatode: Meloidogyne sp.

| Compound of the Invention No. | Concentration of active agent in mg/liter of earth | | |
|---|---|---|---|
| | 200 mg | 100 mg | 50 mg |
| 3 | 100 | 100 | 92 |
| 4 | 100 | 100 | 98 |
| 21 | 100 | 100 | 100 |
| 22 | 100 | 100 | 100 |
| 23 | 100 | 100 | 93 |
| 24 | 100 | 100 | 100 |
| 25 | 100 | 98 | 50 |
| 26 | 100 | 97 | 96 |
| 27 | 100 | 100 | 98 |
| 28 | 100 | 93 | 63 |
| 29 | 100 | 99 | 57 |
| 30 | 100 | 100 | 71 |
| 31 | 100 | 97 | 93 |
| 32 | 99 | 98 | — |
| 33 | 100 | 100 | 95 |
| 34 | 92 | 69 | 42 |
| 35 | 95 | 95 | 64 |
| 36 | 100 | 99 | 93 |
| 37 | 100 | 99 | — |
| 38 | 97 | 53 | — |
| 44 | 100 | 100 | — |
| 52 | 93 | 97 | 81 |
| 59 | 100 | 95 | — |
| 63 | 100 | 42 | — |

EXAMPLE 23

Leaf Treatment of Grapevines Against Plasmopara Viticola

Young grapevines having 5 to 8 leaves were treated so as to be dripping wet with the compounds listed in Table XIX at the concentration also indicated so as to be dripping wet. After drying of the spray deposits the bottom side of the leaves was sprayed with an aqueous suspension of sporangia of the fungus (about 20,000 per ml). The plants were then immediately subjected to incubation in a hothouse at a temperature of 22° to 24° C. and in a maximum humidity atmosphere. Starting with the second day the air humidity was reduced for 3 to 4 days to a normal level (30 to 70% saturation) and was then kept for 1 day on a water vapor saturation. Subsequently, the percentage portion of fungus infected surface was determined for each leaf and the average was calculated for each treatment to determine the fungicidal action on the bases of the following equation:

$$100 - \frac{100 \cdot \text{infestation in treated plants}}{\text{infestation in untreated plants}} = \% \text{ action}$$

TABLE XIX

| Compound of the Invention No. | % of active agent | % activity |
|---|---|---|
| 71 | 0.025 | 48 |
| 128 | 0.025 | 100 |
| 130 | 0.025 | 75 |
| 132 | 0.025 | 92 |
| 133 | 0.025 | 77 |
| 134 | 0.025 | 83 |
| 139 | 0.025 | 91 |
| 140 | 0.025 | 99 |
| 141 | 0.025 | 98 |
| 142 | 0.025 | 99 |

EXAMPLE 24

Leaf Treatment of Squash Plants Against Erysiphe Cichoracearum

Young squash plants were sprayed dripping wet with the compounds listed in Table XX below and at the concentration indicated. After drying of the spray deposit the plants were inoculated by dusting with dry mildew spores of *Erysiphe cichoracearum*. The incubation was carried out at 24° C. and after a week the surface infested with mildew was determined in percentage relative to the total leaf surface.

The fungicidal activity was calculated as follows:

$$100 - \frac{100 \cdot \text{infestation in treated plants}}{\text{infestation in untreated plants}} = \% \text{ activity}$$

TABLE XX

| Compound of the Invention No. | % of active material | % activity |
|---|---|---|
| 67 | 0.025 | 97 |
| 68 | 0.025 | 85 |
| 72 | 0.025 | 90 |
| 74 | 0.025 | 100 |
| 78 | 0.025 | 90 |
| 103 | 0.025 | 70 |
| 146 | 0.025 | 92 |
| 147 | 0.025 | 94 |
| 154 | 0.025 | 90 |

TABLE 25

Seed Treatment of Oats on Acres in the Open Air Against Ustilago Avenae

Oat seed material was dipped into a suspension of the spores of Ustilago avenae which is the agent causing the oat smuts. The seed material was then exposed in a vacuum desiccator to a repeated change from atmospheric to subatmospheric pressure. After drying of the seed material the material was treated with the compounds stated in Table XXI below which were applied as a powdery composition. Ten weeks after seeding the diseased panicles were counted and the activity was calculated according to the formula $$100 - \frac{100 \cdot \text{infestation in treated plants}}{\text{infestation in untreated plants}} = \% \text{ activity}$$

TABLE XXI

| Compound of the Invention No. | g of active agent per 100 kg | % activity |
|---|---|---|
| 29 | 10 | 55 |
|  | 20 | — |
| 59 | 10 | 82 |
|  | 20 | — |
| 63 | 10 | 70 |
|  | 20 | — |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. 1,2,3-triazole carboxylic acid amides of the formula

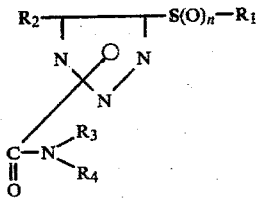

in which
  $R_1$ is $C_1$–$C_{10}$-alkyl, $C_2$–$C_8$-alkenyl or alkinyl or is aryl-$C_1$–$C_3$-alkyl which may be substituted in one or several places by $C_1$–$C_6$-alkyl and/or halogen and/or $C_1$–$C_6$-alkoxy and/or nitro and/or trifluoromethyl,
  $R_2$ is hydrogen or $C_1$–$C_{10}$ alkyl in which the chain may be interrupted in one or several places by oxygen- or sulfur atoms and which may be substituted by halogen,
  $R_3$ and $R_4$ are the same or different and are hydrogen, $C_1$–$C_{10}$ alkyl, $C_1$–$C_{10}$ alkyl which is substituted by halogen or $C_1$–$C_3$-alkoxy, $C_2$–$C_8$-alkenyl or alkinyl, aryl-$C_1$–$C_3$-alkyl which may be substituted in one or several places by $C_1$–$C_6$-alkyl and/or halogen and/or $C_1$–$C_6$-alkoxy and/or nitro and/or trifluoromethyl, a $C_3$–$C_8$ cyclo aliphatic hydrocarbon group which may also be substituted in one or several places by $C_1$–$C_6$-alkyl, or an aromatic hydrocarbon group which may be substituted in one or several places by $C_1$–$C_6$ alkyl and/or halogen and/or $C_1$–$C_6$-alkoxy and/or nitro and/or trifluoromethyl, or wherein
  $R_3$ and $R_4$ together with the adjoining nitrogen atom conconstitute a 3 to 7-member ring which may include further oxygen, sulfur or nitrogen atoms and wherein n is 0, 1 or 2,
or an isomeric mixture from any of the listed compounds.

2. The 1,2,3-triazole carboxylic acid amides of claim 1 wherein
  $R_1$ is alkyl of 1 carbon atom or is aryl-$C_1$–$C_3$-alkyl which may be substituted by chlorine,
  $R_2$ is hydrogen, methyl, ethyl, propyl, isopropyl, butyl or tert.-butyl,
  $R_3$ is alkyl, alkenyl or alkinyl of up to 6 carbon atoms or cyclo alkyl and which groups may be substituted by chlorine or methoxy,
  $R_4$ is alkyl, alkenyl or alkinyl with up to 6 carbon atoms or cyclo alkyl which may be substituted by chlorine or methoxy or is aryl-$C_1$–$C_3$-alkyl which may be substituted by chlorine or methyl, or is an aromatic hydrocarbon group which may be substituted by halogen or methyl or wherein
  $R_3$ and $R_4$ together with the adjoining nitrogen atom form a morpholino-, piperidino-, pyrrolidino- or hexamethylenimino group, and wherein
n is 2.

3. The 1,2,3-triazole carboxylic acid amides of claim 1 wherein
  $R_1$ is methyl, ethyl, propyl, allyl or propino-2-yl,
  $R_2$ is hydrogen, methyl, ethyl, propyl, butyl or tert.-butyl,
  $R_3$ is hydrogen or methyl,
  $R_4$ is methyl and wherein
n is 0.

4. The 1,2,3-triazole carboxylic acid amides of claim 1 wherein
  $R_1$ is alkyl of 1 to 10 carbon atoms, allyl, 2-methylallyl, propino-2-yl or aryl-$C_1$–$C_3$-alkyl, which latter may be substituted by chlorine,
  $R_2$ is hydrogen, methyl, ethyl, propyl, isopropyl, butyl, sec.-butyl, isobutyl, or tert.-butyl,
  $R_3$ is hydrogen, alkyl, alkenyl or alkinyl of up to 6 carbon atoms,
  $R_4$ is alkyl, alkenyl or alkinyl of up to 6 carbon atoms, and wherein
n is 0.

5. The composition of claim 1 which is 4-propylsulfonyl-1,2,3-triazole-1(2,3)-carboxylic acid dipropylamide.

6. The composition of claim 1 which is 4-methyl-5-methylthio-1,2,3-triazole-1(2,3)-carboxylic acid dimethylamide.

7. The composition of claim 1 which is 4-methylthio-1,2,3-triazole-1(2,3)-carboxylic acid methylamide.

8. The composition of claim 1 which is 4-methylthio-1,2,3-triazole-1(2,3)-carboxylic acid anilide.

9. The composition of claim 1 which is 4-methylthio-1,2,3-triazole-1(2,3)-carboxylic acid ethylamide.

10. The composition of claim 1 which is 4-methylthio-1,2,3-triazole-1(2,3)-carboxylic acid propylamide.

11. The composition of claim 1 which is 4-methylthio-1,2,3-triazole-1(2,3)-carboxylic acid butylamide.

12. The composition of claim 1 which is 4-methylthio-1,2,3-triazole-1(2,3)-carboxylic acid cyclohexylamide.

13. The composition of claim 1 which is 4-methylthio-1,2,3-triazole-1(2,3)-carboxylic acid (2-methylanilide).

14. The composition of claim 1 which is 4-methylthio-1,2,3-triazole-1(2,3)-carboxylic acid-(2-chloroanilide).

15. The composition of claim 1 which is 4-methylthio-1,2,3-triazole-1(2,3)-carboxylic acid (3-methylanilide).

16. The composition of claim 1 which is 4-methylthio-1,2,3-triazole-1(2,3)-carboxylic acid (4-methylanilide).

17. The composition of claim 1 which is 4-methylthio-1,2,3-triazole-1(2,3)-carboxylic acid-(3-chloroanilide).

18. The composition of claim 1 which is 4-methylthio-1,2,3-triazole-1(2,3)-carboxylic acid-(4-chloroanilide).

19. The composition of claim 1 which is 4-methylthio-1,2,3-triazole-1(2,3)carboxylic acid-allylamide.

20. The composition of claim 1 which is 4-methylthio-1,2,3-triazole-1(2,3)-carboxylic acid dimethylamide.

21. The composition of claim 1 which is 4-ethylthio-1,2,3-triazole-1(2,3)-carboxylic acid methylamide.

22. The composition of claim 1 which is 4-propylthio-1,2,3-triazole-1(2,3)-carboxylic acid methylamide.

23. The composition of claim 1 which is 4-isopropylthio-1,2,3-triazole-1(2,3)-carboxylic acid methylamide.

24. The composition of claim 1 which is 4-butylthio-1,2,3-triazole-1(2,3)-carboxylic acid methylamide.

25. The composition of claim 1 which is 4-(1-methylpropylthio)-1,2,3-triazole-1(2,3)-carboxylic acid methylamide.

26. The composition of claim 1 which is 4-allylthio-1,2,3-triazole-1(2,3)-carboxylic acid methylamide.

27. The composition of claim 1 which is 4-isobutylthio-1,2,3-triazole-1(2,3)-carboxylic acid methylamide.

28. The composition of claim 1 which is 4-(2-propinylthio)-1,2,3-triazole-1(2,3)-carboxylic acid methylamide.

29. The composition of claim 1 which is 4-benzylthio-1,2,3-triazole-1(2,3)-carboxylic acid methylamide.

30. The composition of claim 1 which is 4-methylsulfonyl-1,2,3-triazole-1(2,3)-carboxylic acid dimethylamide.

31. The composition of claim 1 which is 4-methylsulfonyl-1,2,3-triazole-1(2,3)-carboxylic acid methylamide.

32. The composition of claim 1 which is 4-methylsulfonyl-1,2,3-triazole-1(2,3)-carboxylic acid ethylamide.

33. The composition of claim 1 which is 4-methylsulfonyl-1,2,3-triazole-1(2,3)-carboxylic acid propylamide.

34. The composition of claim 1 which is 4-methylsulfonyl-1,2,3-triazole-1(2,3)-carboxylic acid butylamide.

35. The composition of claim 1 which is 4-methylsulfinyl-1,2,3-triazole-1(2,3)-carboxylic acid methylamide.

36. The composition of claim 1 which is 4-methylsulfinyl-1,2,3-triazole-1(2,3)-carboxylic acid ethylamide.

37. The composition of claim 1 which is 4-methylsulfinyl-1,2,3-triazole-1(2,3)-carboxylic acid propylamide.

38. The composition of claim 1 which is 4-methylsulfonyl-1,2,3-triazole-1(2,3)-carboxylic acid anilide.

39. The composition of claim 1 which is 4-methylsulfonyl-1,2,3-triazole-1(2,3)-carboxylic acid cyclohexlamide.

40. The composition of claim 1 which is 4-methylsulfonyl-1,2,3-triazole-1(2,3)-carboxylic acid-(4-chloroanilide).

41. The composition of claim 1 which is 4-methylsulfonyl-1,2,3-triazole-1(2,3)-carboxylic acid-(4-methylanilide).

42. The composition of claim 1 which is 4-methylsulfonyl-1,2,3-triazole-1(2,3)-carboxylic acid-allylamide.

43. The composition of claim 1 which is 4-methyl-5-methylthio-1,2,3-triazole-1(2,3)-carboxylic acid methylamide.

44. The composition of claim 1 which is 4-methylsulfinyl-1,2,3-triazole-1(2,3)-carboxylic acid butylamide.

45. The composition of claim 1 which is 4-methylsulfinyl-1,2,3-triazole-1(2,3)-carboxylic acid-(4-methylanilide).

46. The composition of claim 1 which is 4-methylsulfinyl-1,2,3-triazole-1(2,3)-carboxylic acid-(4-chloroanilide).

47. The composition of claim 1 which is 4-methylsulfinyl-1,2,3-triazole-1(2,3)-carboxylic acid allylamide.

48. The composition of claim 1 which is 4-methylsulfinyl-1,2,3-triazole-1(2,3)-carboxylic acid dimethylamide.

49. The composition of claim 1 which is 4-methylsulfonyl-1,2,3-triazole-1(2,3)-carboxylic acid diethylamide.

50. The composition of claim 1 which is 4-isopropylsulfonyl-1,2,3-triazole-1(2,3)-carboxylic acid methylamide.

51. The composition of claim 1 which is 4-isopropylsulfonyl-1,2,3-triazole-1(2,3)-carboxylic acid dimethylamide.

52. The composition of claim 1 which is 4-isopropylsulfonyl-1,2,3-triazole-1(2,3)-carboxylic acid diethylamide.

53. The composition of claim 1 which is 4-propylsulfonyl-1,2,3-triazole-1(2,3)-carboxylic acid methylamide.

54. The composition of claim 1 which is 4-propylsulfonyl-1,2,3-triazole-1(2,3)-carboxylic acid dimethylamide.

55. The composition of claim 1 which is 4-propylsulfonyl-1,2,3-triazole-1(2,3)-carboxylic acid diethylamide.

56. The composition of claim 1 which is 4-propylsulfonyl-1,2,3-triazole-1(2,3)-carboxylic acid ethylamide.

57. The composition of claim 1 which is 4-propylsulfonyl-1,2,3-triazole-1(2,3)-carboxylic acid-(N-ethyl-N-propyl)-amide.

58. The composition of claim 1 which is 4-methylsulfonyl-1,2,3-triazole-1(2,3)-carboxylic acid-(N-ethyl-N-propyl)-amide.

59. The composition of claim 1 which is 4-methylsulfonyl-1,2,3-triazole-1(2,3)-carboxylic acid-N-ethylanilide.

60. The composition of claim 1 which is 4-isopropylsulfonyl-1,2,3-triazole-1(2,3)-carboxylic acid-N-ethylanilide.

61. The composition of claim 1 which is 4-propylsulfonyl-1,2,3-triazole-1(2,3)-carboxylic acid-N-ethylanilide.

62. The composition of claim 1 which is 4-isopropylsulfonyl-1,2,3-triazole-1(2,3)-carboxylic acid-(N-ethyl-N-propyl)-amide.

63. The composition of claim 1 which is 4-butylthio-1,2,3-triazole-1(2,3)-carboxylic acid dimethylamide.

64. The composition of claim 1 which is 4-isobutylthio-1,2,3-triazole-1(2,3)-carboxylic acid dimethylamide.

65. The composition of claim 1 which is 4-butylsulfonyl-1,2,3-triazole-1(2,3)-carboxylic acid dimethylamide.

66. The composition of claim 1 which is 4-butylsulfonyl-1,2,3-triazole-1(2,3)-carboxylic acid diethylamide.

67. The composition of claim 1 which is 4-isobutylsulfonyl-1,2,3-triazole-1(2,3)-carboxylic acid dimethylamide.

68. The composition of claim 1 which is 4-isobutylsulfonyl-1,2,3-triazole-1(2,3)-carboxylic acid diethylamide.
69. The composition of claim 1 which is 4-ethylsulfonyl-1,2,3-triazole-1(2,3)-carboxylic acid dimethylamide.
70. The composition of claim 1 which is 4-ethylsulfonyl-1,2,3-triazole-1(2,3)-carboxylic acid diethylamide.
71. The composition of claim 1 which is 4-(1-methylpropylsulfonyl)-1,2,3-triazole-1(2,3)carboxylic acid dimethylamide.
72. The composition of claim 1 which is 4-benzylsulfonyl-1,2,3-triazole-1(2,3)-carboxylic acid diethylamide.
73. The composition of claim 1 which is 4-butylthio-1,2,3-triazole-1(2,3)-carboxylic acid diethylamide.
74. The composition of claim 1 which is 4-(1-methylpropylsulfonyl)-1,2,3-triazole-1(2,3)-carboxylic acid diethylamide.
75. The composition of claim 1 which is 4-benzylsulfonyl-1,2,3-triazole-1(2,3)-carboxylic acid dimethylamide.
76. The composition of claim 1 which is 4-ethylthio-1,2,3-triazole-1(2,3)-carboxylic acid dimethylamide.
77. The composition of claim 1 which is 4-ethylthio-1,2,3-triazole-1(2,3)-carboxylic acid diethylamide.
78. The composition of claim 1 which is 4-isobutylthio-1,2,3-triazole-1(2,3)-carboxylic acid diethylamide.
79. The composition of claim 1 which is 4-(1-methylpropylthio)-1,2,3-triazole-1(2,3)-carboxylic acid dimethylamide.
80. The composition of claim 1 which is 4-(1-methylpropylthio)-1,2,3-triazole-1(2,3)-carboxylic acid diethylamide.
81. The composition of claim 1 which is 4-benzylthio-1,2,3-triazole-1(2,3)-carboxylic acid dimethylamide.
82. The composition of claim 1 which is 4-benzylthio-1,2,3-triazole-1(2,3)-carboxylic acid diethylamide.
83. The composition of claim 1 which is 4-propylsulfonyl-1,2,3-triazole-1(2,3)-carboxylic acid propylamide.
84. The composition of claim 1 which is 4-propylsulfonyl-1,2,3-triazole-1(2,3)-carboxylic acid butylamide.
85. The composition of claim 1 which is 4-propylsulfonyl-1,2,3-triazole-1(2,3)-carboxylic acid isopropylamide.
86. The composition of claim 1 which is 4-propylsulfonyl-1,2,3-triazole-1(2,3)-carboxylic acid dibutylamide.
87. The composition of claim 1 which is 4-propylsulfonyl-1,2,3-triazole-1(2,3)-carboxylic acid pyrrolidide.
88. The composition of claim 1 which is 4-propylsulfonyl-1,2,3-triazole-1(2,3)-carboxylic acid piperidide.
89. The composition of claim 1 which is 4-propylsulfonyl-1,2,3-triazole-1(2,3)-carboxylic acid diallylamide.
90. The composition of claim 1 which is 4-propylsulfonyl-1,2,3-triazole-1(2,3)-carboxylic acid morpholide.
91. The composition of claim 1 which is 4-butylsulfonyl-1,2,3-triazole-1(2,3)-carboxylic acid-(N-ethyl-N-propyl)-amide.
92. The composition of claim 1 which is 4-isobutylsulfonyl-1,2,3-triazole-1(2,3)-carboxylic acid-(N-ethyl-N-propyl)-amide.
93. The composition of claim 1 which is 4-(1-methylpropylsulfonyl)-1,2,3-triazole-1-(2,3)-carboxylic acid-(N-ethyl-N-propyl)-amide.
94. The composition of claim 1 which is 4-propylsulfonyl-1,2,3-triazole-1(2,3)-carboxylic acid-(N-ethyl-N-butyl)-amide.
95. The composition of claim 1 which is 4-propylsulfonyl-1,2,3-triazole-1(2,3)-carboxylic acid dipentylamide.
96. The composition of claim 1 which is 4-propylsulfonyl-1,2,3-triazole-1(2,3)-carboxylic acid-(N-ethyl-N-cyclohexyl)-amide.
97. The composition of claim 1 which is 4-propylsulfonyl-1,2,3-triazole-1(2,3)-carboxylic acid diisopropylamide.
98. The composition of claim 1 which is 4-ethylsulfonyl-1,2,3-triazole-1(2,3)-carboxylic acid-(N-ethyl-N-propyl)-amide.
99. The composition of claim 1 which is 4-ethylsulfonyl-1,2,3-triazole-1(2,3)-carboxylic acid dipropylamide.
100. The composition of claim 1 which is 4-ethylsulfonyl-1,2,3-triazole-1(2,3)-carboxylic acid dibutylamide.
101. The composition of claim 1 which is 4-butylsulfonyl-1,2,3-triazole-1(2,3)-carboxylic acid dipropylamide.
102. The composition of claim 1 which is 4-butylsulfonyl-1,2,3-triazole-1(2,3)-carboxylic acid dibutylamide.
103. The composition of claim 1 which is 4-(1-methylpropylsulfonyl)-1,2,3-triazole-1(2,3)-carboxylic acid dibutylamide.
104. The composition of claim 1 which is 4-isobutylsulfonyl-1,2,3-triazole-1(2,3)-carboxylic acid dipropylamide.
105. The composition of claim 1 which is 4-isobutylsulfonyl-1,2,3-triazole-1(2,3)-carboxylic acid dibutylamide.
106. The composition of claim 1 which is 4-(1-methylpropyl)-sulfonyl-1,2,3-triazole-1(2,3)-carboxylic acid dipropylamide.
107. The composition of claim 1 which is 4-(1-methylpropyl)-sulfonyl-1,2,3-triazole-1(2,3)-carboxylic acid diisopropylamide.
108. The composition of claim 1 which is 4-butylsulfonyl-1,2,3-triazole-1(2,3)-carboxylic acid-(N-ethyl-N-butyl)-amide.
109. The composition of claim 1 which is 4-isobutylsulfonyl-1,2,3-triazole-1(2,3)-carboxylic acid-(N-ethyl-N-butyl)-amide.
110. The composition of claim 1 which is 4-(1-methylpropyl)-sulfonyl-1,2,3-triazole-1(2,3)-carboxylic acid-(N-ethyl)-N-butyl)-amide.
111. The composition of claim 1 which is 4-ethylsulfonyl-1,2,3-triazole-1(2,3)-carboxylic acid-(N-ethyl-N-cyclohexyl)-amide.
112. The composition of claim 1 which is 4-isopropylsulfonyl-1,2,3-triazole-1(2,3)-carboxylic acid butylamide.
113. The composition of claim 1 which is 4-isopropylsulfonyl-1,2,3-triazole-1(2,3)-carboxylic acid dipropylamide.
114. The composition of claim 1 which is 4-butylsulfonyl-1,2,3-triazole-1(2,3)-carboxylic acid-(N-ethyl-N-cyclohexyl)-amide.
115. The composition of claim 1 which is 4-(1-methylpropyl)-sulfonyl-1,2,3-triazole-1(2,3)-carboxylic acid-(N-ethyl-N-cyclohexyl)-amide.
116. The composition of claim 1 which is 4-propylsulfonyl-1,2,3-triazole-1(2,3)-carboxylic acid diisobutylamide.
117. The composition of claim 1 which is 4-propylsulfonyl-1,2,3-triazole-1(2,3)-carboxylic acid dihexylamide.
118. The composition of claim 1 which is 4-propylsulfonyl-1,2,3-triazole-1(2,3)-carboxylic acid-(N-ethyl-N-benzyl)-amide.

119. The composition of claim 1 which is 4-propylsulfonyl-1,2,3-triazole-1(2,3)-carboxylic acid-(N-ethyl-N-isopropyl)-amide.

120. The composition of claim 1 which is 4-propylsulfonyl-1,2,3-triazole-1(2,3)-carboxylic acid-N,N-hexamethyleneamide.

121. The composition of claim 1 which is 4-propylsulfonyl-1,2,3-triazole-1(2,3)-carboxylic acid-N-(2-cyanoethyl)-anilide.

122. The composition of claim 1 which is 4-propylsulfonyl-1,2,3-triazole-1(2,3)-carboxylic acid-N-methylanilide.

123. The composition of claim 1 which is 4-ethylsulfonyl-1,2,3-triazole-1(2,3)-carboxylic acid-(N-ethyl-N-butyl)-amide.

124. The composition of claim 1 which is 4-isopropylsulfonyl-1,2,3-triazole-1(2,3)-carboxylic acid-(N-ethyl-N-butyl)-amide.

125. The composition of claim 1 which is 4-isobutylsulfonyl-1,2,3-triazole-1(2,3)-carboxylic acid-(N-ethyl-N-cyclohexyl)-amide.

126. The composition of claim 1 which is 4-butylsulfonyl-1,2,3-triazole-1(2,3)-carboxylic acid-(N-ethyl-N-isopropyl)-amide.

127. The composition of claim 1 which is 4-isobutylsulfonyl-1,2,3-triazole-1(2,3)-carboxylic acid-(N-ethyl-N-isopropyl)-amide.

128. The composition of claim 1 which is 4-propylsulfinyl-1,2,3-triazole-1(2,3)-carboxylic acid diethylamide.

129. The composition of claim 1 which is 4-propylsulfonyl-1,2,3-triazole-1(2,3)-carboxylic acid-bis(2-chloroethyl)-amide.

130. The composition of claim 1 which is 4-butylsulfonyl-1,2,3-triazole-1(2,3)-carboxylic acid-N-ethyl-N-benzyl-amide.

131. The composition of claim 1 which is 4-(1-methylpropyl)-sulfonyl-1,2,3-triazole-1(2,3)-carboxylic acid-(N-ethyl-N-benzyl)-amide.

132. The composition of claim 1 which is 4-isobutylsulfonyl-1,2,3-triazole-1(2,3)-carboxylic acid-(N-ethyl-N-benzyl)-amide.

133. The composition of claim 1 which is 4-methylsulfonyl-1,2,3-triazole-1(2,3)-carboxylic acid-(N-ethyl-N-butyl)-amide.

134. The composition of claim 1 which is 4-ethylthio-5-methyl-1,2,3-triazole-1(2,3)-carboxylic acid dimethylamide.

135. The composition of claim 1 which is 4-propylsulfonyl-5-methyl-1,2,3-triazole-1(2,3)-carboxylic acid dipropylamide.

136. The composition of claim 1 which is 4-propylsulfonyl-5-methyl-1,2,3-triazole-1(2,3)-carboxylic acid-(N-ethyl-N-isopropyl)-amide.

137. The composition of claim 1 which is 4-(2-propinylthio)-5-methyo-1,2,3-triazole-1(2,3)-carboxylic acid dimethylamide.

138. The composition of claim 1 which is 4-methylsulfonyl-1,2,3-triazole-1(2,3)-carboxylic acid-(N-ethyl-N-isopropyl)-amide.

139. The composition of claim 1 which is 4-ethylsulfonyl-1,2,3-triazole-1(2,3)-carboxylic acid-(N-ethyl-N-isopropyl)-amide.

140. The composition of claim 1 which is 4-(1-methylpropyl)-sulfonyl-1,2,3-triazole-1(2,3)-carboxylic acid-(N-ethyl-N-isopropyl)-amide.

141. The composition of claim 1 which is 4-ethylsulfonyl-1,2,3-triazole-1(2,3)-carboxylic acid diisopropylamide.

142. The composition of claim 1 which is 4-isobutylsulfonyl-1,2,3-triazole-1(2,3)-carboxylic acid diisopropylamide.

143. The composition of claim 1 which is 4-butylsulfonyl-1,2,3-triazole-1(2,3)-carboxylic acid diisopropylamide.

144. The composition of claim 1 which is 5-methyl-4-propylsulfonyl-1,2,3-triazole-1(2,3)-carboxylic acid diisopropylamide.

145. The composition of claim 1 which is 4-allylthio-5-methyl-1,2,3-carboxylic acid dimethylamide.

146. The composition of claim 1 which is 4-(2-cyanoethylthio)-5-methyl-1,2,3-triazole-1(2,3)-carboxylic acid dimethylamide.

147. The composition of claim 1 which is 4-methylthio-5-propyl-1,2,3-triazole-1(2,3)-carboxylic acid dimethylamide.

148. The composition of claim 1 which is 5-ethyl-4-methylthio-1,2,3-triazole-1(2,3)-carboxylic acid dimethylamide.

149. The composition of claim 1 which is 5-isopropyl-4-methylthio-1,2,3-triazole-1(2,3)-carboxylic acid dimethylamide.

150. The composition of claim 1 which is 5-tert.-butyl-4-methylthio-1,2,3-triazole-1(2,3)-carboxylic acid dimethylamide.

151. The composition of claim 1 which is 4-isopropylthio-5-methyl-1,2,3-triazole-1(2,3)-carboxylic acid dimethylamide.

152. A biocidal composition having herbicidal, insecticidal, acaricidal, fungicidal and/or nematocidal activity comprising about 10 to 80% by weight of the active agents of claim 1 and about 90 to 20% by weight of liquid or solid carrier materials which may include up to about 20% by weight of surface active agents.

* * * * *